United States Patent
Burwinkel et al.

(10) Patent No.: US 9,683,264 B2
(45) Date of Patent: Jun. 20, 2017

(54) CIRCULATING MIRNAS AS EARLY DETECTION MARKER AND PROGNOSTIC MARKER

(71) Applicants: Ruprecht-Karls-Universitat, Heidelberg (DE); Deutsches Krebsforschungszentrum, Heidelberg (DE)

(72) Inventors: Barbara Burwinkel, Heidelberg (DE); Dharanija Madhavan, Heidelberg (DE)

(73) Assignees: DEUTSCHES KREBSFORSCHUNGSZENTRUM, Heidelberg (DE); RUPRECHT-KARLS-UNIVERSITAT, Heidelberg (DE)

( * ) Notice: Subject to any disclaimer, the term of this patent is extended or adjusted under 35 U.S.C. 154(b) by 0 days.

(21) Appl. No.: 14/700,479

(22) Filed: Apr. 30, 2015

(65) Prior Publication Data

US 2015/0315659 A1    Nov. 5, 2015

(30) Foreign Application Priority Data

May 2, 2014    (EP) .................................... 14166923

(51) Int. Cl.
*C12Q 1/68*    (2006.01)
*A61N 5/10*    (2006.01)

(52) U.S. Cl.
CPC ............. *C12Q 1/6886* (2013.01); *A61N 5/10* (2013.01); *C12Q 2600/118* (2013.01); *C12Q 2600/158* (2013.01); *C12Q 2600/16* (2013.01); *C12Q 2600/178* (2013.01)

(58) Field of Classification Search
USPC .......... 435/6, 6.1, 6.12, 91.1, 91.31; 514/44; 536/23.1, 24.31, 24.5
See application file for complete search history.

(56) References Cited

U.S. PATENT DOCUMENTS

| | | | | |
|---|---|---|---|---|
| 2012/0309645 A1* | 12/2012 | Keller | .................. | C12Q 1/6886 506/9 |
| 2013/0035251 A1* | 2/2013 | Keller | .................. | C12Q 1/6886 506/9 |
| 2013/0184175 A1* | 7/2013 | Beaudenon-Huibregtse | .......... | C12Q 1/6886 506/9 |
| 2014/0018411 A1* | 1/2014 | Croce | .................. | C12N 15/111 514/44 A |
| 2014/0031415 A1* | 1/2014 | Brown | .................. | C12N 15/111 514/44 A |

FOREIGN PATENT DOCUMENTS

| | | |
|---|---|---|
| WO | 2010/151133 | 12/2010 |
| WO | WO 2010/151133 | * 12/2010 |
| WO | 2012/040500 | 3/2012 |
| WO | 2013/190091 | 12/2013 |
| WO | WO 2013/190091 | * 12/2013 |

OTHER PUBLICATIONS

European Search Report dated Dec. 15, 2014 from European Patent Application No. 14166923.4, pp. 1-13.
Song, Su Jung et al. MicroRNA-Antagonism Regulates Breast Cancer Stemness and Metastasis via TET-Family-Dependent Chromatin Remodeling. Cell, Jul. 18, 2013, vol. 154, No. 2, pp. 311-324.
Franchina, Tindara et al., Circulating miR-22, miR24, and miR-34a as Novel Predictive Biomarkers to Pemetrexed-Base Chemotherapy in Advanced Non-Small Cell Lung Cancer. Journal of Cellular Physiology, Jun. 1, 2013, pp. 97-99.
Shin, Yoon Mi et al. Diagnostic Value of Circulating Extracellular miR-34, miR-185, and miR-22 Levels in Lung Adenocarcinoma-Associated Malignant Pleural Effusion. Cancer Research and Treatment, Apr. 1, 2014, vol. 26, No. 2, pp. 178-185.

* cited by examiner

*Primary Examiner* — Jane Zara
(74) *Attorney, Agent, or Firm* — MH2 Technology Law Group, LLP

(57) ABSTRACT

Provided is a novel method for the early detection and/or discrimination of cancer and anti-cancer agents for the prevention or early treatment of cancer. In particular, the method relates to the determination of levels of circulating miRNAs in breast cancer patients, both primary and metastatic. Furthermore, kits, devices, pharmaceutical compositions as well as methods related thereto are described.

9 Claims, 26 Drawing Sheets

|  | Good Prognosis PFS > 16 months | Bad Prognosis PFS < 3 months | Total |
| --- | --- | --- | --- |
| Number of Patients | 20 | 20 | 40 |
| Mean Age | 60.8 | 56.3 | - |
| CTCpos-MBC | 2 | 13 | 15 |
| CTCneg-MBC | 9 | 6 | 15 |
| CTClow-MBC | 9 | 1 | 10 |
| With bone metastasis | 13 | 13 | 29 |
| With liver metastasis | 7 | 9 | 16 |
| With lung metastasis | 4 | 5 | 8 |
| Patient died | 2 | 10 | 12 |
| Histology- IDC | 8 | 9 | 17 |
| Histology- ILC | 4 | 3 | 7 |
| ER positive | 14 | 12 | 26 |
| PR positive | 11 | 8 | 19 |
| HER2 positive | 4 | 5 | 9 |

FIG. 8

| Clinical Characteristic | | MBC$_{BL}$ (n=237) | MBC$_{IC}$ (n=119) |
|---|---|---|---|
| Age | Mean | 59.7 | 62 |
| | Median | 59 | 63 |
| | Range | 29-89 | 43-84 |
| Bone | Yes | 152 | 51 |
| | No | 80 | 24 |
| | NA | 0 | 0 |
| Liver | Yes | 100 | 37 |
| | No | 132 | 38 |
| | NA | 0 | 0 |
| Lung | Yes | 82 | 27 |
| | No | 150 | 48 |
| | NA | 0 | 0 |
| No of sites of Metastasis | 1-2 | 117 | 36 |
| | 3-5 | 108 | 34 |
| | >5 | 7 | 5 |
| | NA | 0 | 0 |
| Disseminated Metastasis | Yes | 123 | 38 |
| | No | 109 | 37 |
| | NA | 0 | 0 |
| ER Status | Positive | 74 | 20 |
| | Negative | 31 | 11 |
| | NA | 127 | 44 |
| PR Status | Positive | 55 | 15 |
| | Negative | 50 | 17 |
| | NA | 127 | 43 |
| HER2 Status | Positive | 27 | 10 |
| | Negative | 84 | 25 |
| | NA | 121 | 40 |
| Therapy lines given | 0-1 | 87 | 27 |
| | 2-4 | 105 | 32 |
| | >4 | 39 | 16 |
| | NA | 1 | 0 |
| Radiotherapy | Yes | 110 | 41 |
| | No | 121 | 34 |
| | NA | 1 | 0 |
| Endocrine Therapy | Yes | 139 | 45 |
| | No | 92 | 30 |
| | NA | 1 | 0 |
| Antibody Therapy | Yes | 107 | 34 |
| | No | 124 | 41 |
| | NA | 1 | 0 |

FIG. 9A

| Clinical Characteristic | | MBC$_{BL}$ | MBC$_{IC}$ |
|---|---|---|---|
| PFS | Progression | 183 | 61 |
| | No Progression | 37 | 11 |
| | Median (in months) | 5 | 5 |
| | NA | 12 | 3 |
| OS | Dead | 84 | 28 |
| | Alive | 145 | 47 |
| | Median (in months) | 13 | 13 |
| | NA | 3 | 0 |
| Histology[a] | IDC | 128 | 37 |
| | ILC | 19 | 6 |
| | Others | 4 | 1 |
| | NA | 81 | 31 |
| T[a] | T0/T1 | 78 | 24 |
| | T2 | 99 | 32 |
| | T3 | 22 | 6 |
| | T4 | 23 | 7 |
| | NA | 10 | 6 |
| N[a] | N0 | 74 | 20 |
| | N1 | 80 | 24 |
| | N2 | 23 | 13 |
| | N3 | 32 | 9 |
| | NA | 23 | 9 |
| M[a] | M0 | 110 | 34 |
| | M1 | 46 | 12 |
| | NA | 76 | 29 |
| Grading[a] | G1 | 5 | 1 |
| | G2 | 96 | 27 |
| | G3 | 95 | 37 |
| | NA | 36 | 10 |
| ER[a] | Pos | 156 | 48 |
| | Neg | 65 | 23 |
| | NA | 11 | 4 |
| PR[a] | Pos | 137 | 41 |
| | Neg | 80 | 28 |
| | NA | 15 | 6 |
| HER2[a] | Pos | 44 | 15 |
| | Neg | 155 | 51 |
| | NA | 33 | 9 |
| DDFS[a] | Median (in months) | 49 | 49 |

FIG. 9B

| Poor vs Good Prognosis | | | Dead vs Alive | | |
|---|---|---|---|---|---|
| miRNA | P-value | FC | miRNA | P-value | FC |
| miR-22 | 0.006 | 93.638 | miR-618 | 0.0002 | 0.046 |
| miR-149 | 0.012 | 27.811 | miR-429 | 0.0002 | 18.933 |
| miR-200b | 0.016 | 5.923 | miR-141 | 0.0002 | 5.667 |
| miR-144 | 0.018 | 0.448 | miR-149 | 0.0003 | 141.926 |
| miR-770-5p | 0.027 | 55.386 | miR-215 | 0.001 | 0.004 |
| miR-200a | 0.029 | 14.177 | miR-1260 | 0.002 | 72.183 |
| miR-200c | 0.033 | 5.870 | miR-1274A | 0.003 | 3.399 |
| miR-618 | 0.049 | 4.713 | miR-200a | 0.003 | 42.890 |
| | | | miR-200b | 0.007 | 8.366 |
| | | | miR-486-5p | 0.008 | 0.478 |
| | | | miR-146b-3p | 0.011 | 8.876 |
| | | | miR-200c | 0.013 | 9.074 |
| | | | miR-365 | 0.014 | 2.179 |
| | | | miR-203 | 0.019 | 2.590 |
| | | | miR-193b | 0.024 | 2.156 |
| | | | miR-144 | 0.031 | 0.452 |
| | | | miR-22 | 0.036 | 45.211 |
| | | | miR-758 | 0.040 | 0.460 |
| | | | miR-375 | 0.044 | 2.537 |
| | | | miR-206 | 0.044 | 0.373 |
| | | | miR-34a* | 0.049 | 2.291 |

FIG. 10

| miRNA | MBC$_{BL}$ | | | | | | MBC$_{1C}$ | | | | | |
|---|---|---|---|---|---|---|---|---|---|---|---|---|
| | PFS | | OS | | | | PFS | | | OS | | |
| | HR (95%CI) | P | HR (95%CI) | P | | | HR (95%CI) | P | | HR (95%CI) | P | |
| miR-22 | 1.1 (0.79-1.55) | 0.59 | 1.57 (0.99-2.51) | 0.05 | | | 0.74 (0.45-1.23) | 0.24 | | 1.05 (0.48-2.32) | 0.90 | |
| miR-141 | 1.51 (1.09-2.08) | 0.01 | 3.04 (1.96-4.72) | 1.2E-07 | | | 2.37 (1.47-3.81) | 2.1E-04 | | 8.85 (4.47-17.52) | 1.2E-14 | |
| miR-144 | 0.68 (0.49-0.96) | 0.02 | 0.53 (0.31-0.92) | 0.02 | | | 0.69 (0.43-1.12) | 0.13 | | 0.59 (0.26-1.34) | 0.20 | |
| miR-193b | 1.85 (1.34-2.56) | 0.0001 | 2.62 (1.69-4.07) | 4.1E-06 | | | 1.64 (1.01-2.66) | 0.04 | | 2.77 (1.4-5.5) | 0.002 | |
| miR-200a | 1.44 (1.04-2.01) | 0.03 | 3.56 (2.31-5.5) | 4.6E-10 | | | 1.89 (1.17-3.07) | 0.01 | | 7.67 (3.9-15.1) | 9.7E-13 | |
| miR-200b | 1.6 (1.15-2.22) | 0.004 | 3.21 (2.07-4.98) | 2.1E-08 | | | 2.05 (1.29-3.26) | 1.6E-03 | | 5.92 (3.02-11.6) | 2.3E-09 | |
| miR-200c | 1.62 (1.17-2.23) | 0.003 | 2.32 (1.5-3.6) | 6.6E-05 | | | 2.61 (1.65-4.12) | 1.4E-05 | | 5.62 (2.87-11.02) | 7.9E-09 | |
| miR-203 | 1.41 (1.02-1.94) | 0.04 | 2.17 (1.38-3.42) | 4.9E-04 | | | 1.68 (1.05-2.68) | 0.03 | | 3.44 (1.74-6.8) | 1.4E-04 | |
| miR-210 | 1.23 (0.88-1.72) | 0.219 | 1.77 (1.12-2.78) | 0.01 | | | 1.37 (0.85-2.2) | 0.20 | | 3.24 (1.62-6.47) | 3.6E-04 | |
| miR-215 | 0.59 (0.41-0.84) | 0.002 | 0.58 (0.33-1.01) | 0.05 | | | 0.75 (0.45-1.25) | 0.27 | | 0.89 (0.39-2.04) | 0.78 | |
| miR-365 | 1.12 (0.8-1.57) | 0.495 | 2.01 (1.28-3.17) | 0.002 | | | 1.09 (0.68-1.75) | 0.73 | | 1.09 (0.5-2.41) | 0.82 | |
| miR-375 | 1.4 (1.02-1.93) | 0.04 | 2.42 (1.56-3.76) | 4.3E-05 | | | 1.62 (1.02-2.58) | 0.04 | | 3.81 (1.94-7.51) | 2.3E-05 | |
| miR-429 | 1.58 (1.15-2.17) | 0.004 | 3.47 (2.25-5.30) | 1.2E-09 | | | 2.5 (1.57-3.98) | 3.8E-05 | | 7.37 (3.76-14.45) | 2.4E-12 | |
| miR-486-5p | 0.76 (0.54-1.07) | 0.109 | 0.5 (0.28-0.91) | 0.02 | | | 0.82 (0.5-1.34) | 0.43 | | 0.69 (0.29-1.67) | 0.41 | |
| miR-801 | 1.4 (1.01-1.95) | 0.04 | 2.85 (1.85-4.4) | 6.40E-07 | | | 0.98 (0.61-1.58) | 0.93 | | 3.04 (1.55-5.99) | 6.5E-04 | |
| miR-1260 | 0.92 (0.65-1.29) | 0.613 | 1.98 (1.26-3.12) | 0.002 | | | 0.92 (0.57-1.49) | 0.73 | | 1.41 (0.68-2.95) | 0.36 | |
| miR-1274a | 1.49 (1.08-2.06) | 0.01 | 3.04 (1.96-4.71) | 1.3E-07 | | | 2.29 (1.43-3.66) | 3.4E-04 | | 5.25 (2.67-10.33) | 4.7E-08 | |
| CTC status | 1.52 (1.12-2.06) | 0.006 | 2.9 (1.9-4.4) | 1.9E-07 | | | 1.71 (1.08-2.68) | 0.02 | | 4.65 (2.22-9.78) | 6.9E-06 | |

FIG. 11

| miRNA | P-value | FC |
|---|---|---|
| miR-22 | 2.09E-03 | 1.11 |
| miR-141 | 7.09 | 1.41E-09 |
| miR-144 | 0.75 | 0.16 |
| miR-193b | 1.09 | 0.02 |
| miR-200a | 9.05 | 3.90E-13 |
| miR-200b | 1.93 | 1.21E-03 |
| miR-200c | 2.07 | 2.79E-04 |
| miR-203 | 2.30 | 3.45E-08 |
| miR-210 | 2.12 | 4.95E-08 |
| miR-215 | 0.88 | 0.34 |
| miR-365 | 1.18 | 0.04 |
| miR-375 | 2.26 | 9.66E-07 |
| miR-429 | 1.51 | 0.04 |
| miR-486-5p | 1.11 | 0.22 |
| miR-801 | 4.59 | 1.01E-10 |
| miR-1260 | 1.17 | 0.26 |
| miR-1274a | 2.04 | 3.17E-04 |

FIG. 12

|  | Model | PFS | | OS | |
|---|---|---|---|---|---|
|  |  | Variables | IPE | Variables | IPE |
| Study baseline- MBC_BL | Null model | None | 2.075 | None | 1.351 |
|  | miRNA model | miR-141, miR-144, miR-193b, miR-200b, miR-200c, miR-203, miR-215, miR-429, miR-801, miR-1274a | 2.050 | miR-141, miR-144, miR-193b, miR-200a, miR-200b, miR-215, miR-429, miR-486-5p, miR-801, miR-1260, miR-1274a | 1.347 |
|  | CTC | CTC status | 2.058 | CTC status | 1.457 |
|  | miRNA+CTC (unpenalised) | miR-144, miR-193b, miR-200c, miR-215, miR-1274a, CTC status | 2.036 | miR-141, miR-144, miR-193b, miR-200a, miR-200b, miR-215, miR-429, miR-801, miR-1274a, CTC status | 1.375 |
|  | miRNA+CTC, adjusted for interaction | miR-144, miR-193b, miR-200b, miR-200c, miR-215, miR-429, miR-1274a, miR-1274a:CTC status, CTC status | 2.052 | miR-141, miR-144, miR-200a, miR-200b, miR-215, miR-429, miR-486-5p, miR-801, miR-1274a, miR-1274a:CTC, CTC status | 1.378 |
| After Therapy-MBC_1C | Null model | None | 2.271 | None | 1.318 |
|  | miRNA model | miR-141, miR-200c, miR-429 miR-1274a | 2.160 | miR-141, miR-200a, miR-200b, miR-429, miR-1274a | 0.854 |
|  | CTC | CTC status | 2.300 | CTC status | 1.202 |
|  | miRNA+CTC (unpenalised) | miR-200c, miR-429 miR-1274a , CTC status | 2.197 | miR-141, miR-200a, miR-200b, miR-429, miR-1274a,CTC status | 0.898 |
|  | miRNA+CTC, adjusted for interaction | miR-200c, miR-429,, miR-1274a, miR-141:CTC status, miR-1274a:CTC status | 2.220 | miR-141, miR-200a,, miR-429, miR-1274a, miR-210:CTC status | 0.900 |

FIG. 13

| miRNA | Logrank Analysis- OS | | Metastatic Onset | |
|---|---|---|---|---|
| | HR | *P* | FC | *P* |
| miR-141 | 0.99 (0.68-1.45) | 0.96 | 0.96 | 0.50 |
| miR-144 | 0.64 (0.44-0.94) | 0.02 | 0.78 | 0.07 |
| miR-193b | 1.41 (0.96-2.08) | 0.08 | 1.20 | 0.40 |
| miR-200a | 2.77 (1.82-4.2) | 5.9E-07 | 1.50 | 1.4E-08 |
| miR-200b | 1.92 (1.29-2.86) | 0.001 | 1.61 | 0.006 |
| miR-200c | 1.72 (1.16-2.55) | 0.006 | 1.15 | 0.02 |
| miR-203 | 0.79 (0.54-1.16) | 0.23 | 0.63 | 0.07 |
| miR-210 | 1.8 (1.21-2.66) | 0.003 | 1.13 | 0.05 |
| miR-215 | 0.53 (0.35-0.78) | 0.001 | 0.72 | 0.01 |
| miR-365 | 0.74 (0.5-1.08) | 0.12 | 0.99 | 0.58 |
| miR-375 | 1.2 (0.82-1.76) | 0.34 | 1.25 | 0.73 |
| miR-429 | 1.13 (0.77-1.66) | 0.52 | 0.96 | 0.93 |
| miR-486-5p | 2.65 (1.75-4) | 1.4E-06 | 1.77 | 1.1E-05 |
| miR-801 | 1.33 (0.91-1.95) | 0.14 | 1.16 | 0.79 |
| miR-1260 | 1.18 (0.81-1.73) | 0.39 | 1.15 | 0.07 |
| miR-1274a | 0.84 (0.57-1.23) | 0.36 | 0.89 | 0.81 |

FIG. 14

| miRNA | PFS | | | OS | | |
|---|---|---|---|---|---|---|
| | Cox-HR | Cox-P | Logrank | Cox-HR | Cox-P | Logrank |
| miR-22 | 1 | 0.57 | 0.461 | 0.84 | 0.06 | 0.06 |
| miR-144 | 1.1 | 0.03 | 0.0214 | 1.1 | 0.15 | 0.04 |
| miR-193b | 0.9 | 0.02 | 0.000188 | 0.77 | 1.09E-05 | 9.08E-07 |
| miR-215 | 1.1 | 0.21 | 0.00522 | 1 | 0.65 | 0.05 |
| miR-365 | 0.89 | 0.01 | 0.35 | 0.78 | 4.08E-05 | 0.000853 |
| miR-429 | 0.92 | 0.01 | 0.00477 | 0.81 | 1.94E-07 | 1.06E-08 |
| miR-486-5p | 1 | 0.99 | 0.163 | 1.1 | 0.43 | 0.04 |
| miR-1260 | 0.99 | 0.88 | 0.523 | 0.71 | 0.000183 | 0.00141 |
| miR-1274a | 0.91 | 0.001 | 0.00647 | 0.81 | 6.69E-08 | 7.36E-07 |

FIG. 15A

| miRNA | PFS | | | OS | | |
|---|---|---|---|---|---|---|
| | Cox-HR | Cox-P | Logrank | Cox-HR | Cox-P | Logrank |
| miR-22 | 1.1 | 0.37 | 0.24 | 1.1 | 0.75 | 0.80 |
| miR-144 | 1.1 | 0.05 | 0.07 | 0.77 | 0.33 | 0.36 |
| miR-193b | 0.86 | 0.02 | 0.06 | 1.2 | 2.66E-03 | 1.87E-03 |
| miR-215 | 1.1 | 0.08 | 0.31 | 0.9 | 0.06 | 0.85 |
| miR-365 | 0.93 | 0.29 | 0.82 | 0.73 | 0.31 | 0.96 |
| miR-429 | 0.81 | 6.86E-06 | 6.24E-06 | 1.2 | 4.40E-07 | 7.88E-13 |
| miR-486-5p | 1.2 | 0.03 | 0.23 | 0.96 | 0.13 | 0.47 |
| miR-1260 | 1 | 0.91 | 0.81 | 0.57 | 0.75 | 0.30 |
| miR-1274a | 0.75 | 9.14E-06 | 1.13E-05 | 1.1 | 1.48E-10 | 2.17E-10 |

FIG. 15B

| miRNA | Cox-HR | Cox-P | Logrank |
|---|---|---|---|
| miR-193b | 0.83 | 0.05 | 0.10 |
| miR-215 | 1.1 | 0.41 | 0.58 |
| miR-429 | 0.91 | 0.23 | 0.59 |
| miR-1260 | 0.74 | 4.45E-03 | 0.02 |
| miR-1274a | 0.78 | 1.30E-02 | 2.33E-03 |

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: miR-144; hsa-miR-144-3p; Acc. No. MIMAT0000436

<400> SEQUENCE: 1
uacaguauag augauguacu                                                   20

<210> SEQ ID NO 2
<211> LENGTH: 22
<212> TYPE: DNA
<213> ORGANISM: Artificial Sequence
<220> FEATURE:
<223> OTHER INFORMATION: miR-193b; hsa-miR-193b-3p; Acc. No.
      MIMAT0002819

<400> SEQUENCE: 2
aacuggcccu caaagucccg cu                                                22

<210> SEQ ID NO 3
<211> LENGTH: 22
<212> TYPE: DNA
<213> ORGANISM: Artificial Sequence
<220> FEATURE:
<223> OTHER INFORMATION: miR-200a; hsa-miR-200a-3p; Acc. No.
      MIMAT0000682

<400> SEQUENCE: 3
uaacacuguc ugguaacgau gu                                                22

<210> SEQ ID NO 4
<211> LENGTH: 22
<212> TYPE: DNA
<213> ORGANISM: Artificial Sequence
<220> FEATURE:
<223> OTHER INFORMATION: miR-200b; hsa-miR-200b-3p; Acc. No.
      MIMAT0000318

<400> SEQUENCE: 4
uaauacugcc ugguaaugau ga                                                22

<210> SEQ ID NO 5
<211> LENGTH: 23
<212> TYPE: DNA
<213> ORGANISM: Artificial Sequence
<220> FEATURE:
<223> OTHER INFORMATION: miR-200c; hsa-miR-200c-3p; Acc. No.
      MIMAT0000617
```

```
<400> SEQUENCE: 5
uaauacugcc ggguaaugau gga                                          23

<210> SEQ ID NO 6
<211> LENGTH: 22
<212> TYPE: DNA
<213> ORGANISM: Artificial Sequence
<220> FEATURE:
<223> OTHER INFORMATION: miR-203; hsa-miR-203; Acc. No. MIMAT0000264

<400> SEQUENCE: 6
gugaaauguu uaggaccacu ag                                           22

<210> SEQ ID NO 7
<211> LENGTH: 22
<212> TYPE: DNA
<213> ORGANISM: Artificial Sequence
<220> FEATURE:
<223> OTHER INFORMATION: miR-210; hsa-miR-210-3p; Acc. No. MIMAT0000267

<400> SEQUENCE: 7
cugugcgugu gacagcggcu ga                                           22

<210> SEQ ID NO 8
<211> LENGTH: 23
<212> TYPE: DNA
<213> ORGANISM: Artificial Sequence
<220> FEATURE:
<223> OTHER INFORMATION: miR-215; hsa-miR-215-3p; Acc. No. MIMAT0026476

<400> SEQUENCE: 8
ucugucauuu cuuuaggcca aua                                          23

<210> SEQ ID NO 9
<211> LENGTH: 22
<212> TYPE: DNA
<213> ORGANISM: Artificial Sequence
<220> FEATURE:
<223> OTHER INFORMATION: miR-365a; hsa-miR-365a-3p; Acc. No.
      MIMAT0000710

<400> SEQUENCE: 9
uaaugcsccu aaaaauccuu au                                           22

<210> SEQ ID NO 10
<211> LENGTH: 22
<212> TYPE: DNA
<213> ORGANISM: Artificial Sequence
<220> FEATURE:
<223> OTHER INFORMATION: miR-375; hsa-miR-375; Acc. No. MIMAT0000728

<400> SEQUENCE: 10
uuuguucguu cggcucgcgu ga                                           22

<210> SEQ ID NO 11
<211> LENGTH: 22
<212> TYPE: DNA
<213> ORGANISM: Artificial Sequence
<220> FEATURE:
<223> OTHER INFORMATION: miR-429; hsa-miR-429; Acc. No. MIMAT0001536

<400> SEQUENCE: 11
uaauacuguc ugguaaaacc gu                                           22
```

```
<210> SEQ ID NO 12
<211> LENGTH: 22
<212> TYPE: DNA
<213> ORGANISM: Artificial Sequence
<220> FEATURE:
<223> OTHER INFORMATION: miR-486-5p; hsa-miR-486-5p; Acc. No.
      MIMAT0002177

<400> SEQUENCE: 12
uccuguacug agcugccccg ag                                                22

<210> SEQ ID NO 13
<211> LENGTH: 24
<212> TYPE: DNA
<213> ORGANISM: Artificial Sequence
<220> FEATURE:
<223> OTHER INFORMATION: miR-801; hsa-miR-801

<400> SEQUENCE: 13
gauugcucug cgugcggaau cgac                                              24

<210> SEQ ID NO 14
<211> LENGTH: 18
<212> TYPE: DNA
<213> ORGANISM: Artificial Sequence
<220> FEATURE:
<223> OTHER INFORMATION: miR-1260a; hsa-miR-1260a; Acc. No. MIMAT0005911

<400> SEQUENCE: 14
aucccaccuc ugccacca                                                     18

<210> SEQ ID NO 15
<211> LENGTH: 18
<212> TYPE: DNA
<213> ORGANISM: Artificial Sequence
<220> FEATURE:
<223> OTHER INFORMATION: miR-1274a; hsa-miR-1274a

<400> SEQUENCE: 15
gucccuguuc aggcgcca                                                     18

<210> SEQ ID NO 16
<211> LENGTH: 22
<212> TYPE: DNA
<213> ORGANISM: Artificial Sequence
<220> FEATURE:
<223> OTHER INFORMATION: miR-14; hsa-miR-141-3p; Acc. No. MIMAT0000432

<400> SEQUENCE: 16
uaacacuguc ugguaaagau gg                                                22
```

CIRCULATING MIRNAS AS EARLY DETECTION MARKER AND PROGNOSTIC MARKER

CROSS REFERENCE TO RELATED APPLICATIONS

This application claims priority to and the benefit of European Patent Application No. 14 166 923.4 filed on 2 May 2014, the entire contents of which are incorporated herein by reference.

SEQUENCE LISTING

The instant application contains a. Sequence Listing which has been submitted electronically in ASCII format and is hereby incorporated by reference in its entirety. Said ASCII copy, created on 27 Apr. 2015, is named MFS-124_SL.txt and is 4 kilobytes in size.

FIELD OF THE INVENTION

The present invention generally relates to methods for the early detection, prognostication and prediction of the onset of metastasis cancer, preferably in a primary breast cancer patient or the progression-free survival (PFS) or overall survival (OS) of a patient with metastatic breast cancer. In particular, the present invention provides an expression profile of miRNAs in plasma as a marker for the early detection, prognostication and prediction of breast cancer, as well as anti-cancer prophylactic and early treatment regimens based on the status of expression of said miRNAs in a subject suspected to develop cancer or having cancer at an early stage. The present invention provides a method for monitoring the therapy of a patient being treated against primary breast cancer or metastatic breast cancer as well as anti-cancer agents for use in the prevention, amelioration or treatment of the onset of metastasis in a primary breast cancer patient based on the presence, absence or altered level of the at least one miRNA. Further, the present invention provides a method of dosing the anti-cancer agent for use in the prevention or treatment of metastatic breast cancer as well as a kit for the prediction of the onset of metastasis in a primary breast cancer patient or the progression-free survival (PFS) or overall survival (OS) of a patient with metastatic breast cancer.

BACKGROUND OF THE INVENTION

Cancer is one of the most important medical and health problems in the world. As the leading cause of death worldwide, there were 12.4 million new cancer cases and 7.6 million cancer related deaths in 2008[1]. It has been predicted that the deaths from cancer worldwide will continuously rise and 12 million deaths would be caused by cancer in the year of 2030[1]. Breast cancer (BC) is the most common cancer and the leading cause of cancer-related mortality among women[2], with 1.38 million new cases and 458,000 deaths in 2008[3]. Although therapeutic advances have improved, most BC patients still suffer from greatly reduced quality of life or even metastasis due to delayed diagnosis[2, 4]. Although recent genome-wide association studies (GWAS) have successfully detected several genetic variants associated with the risk of BC, no valuable marker for the early detection of BC has been identified. As an early event in the development of cancer, the onset of metastasis in particular in a primary breast cancer patient or the progression-free survival (PFS) or overall survival (OS) of a patient with metastatic breast cancer seems to be a particularly promising tool.

Breast cancer (BC) and specifically metastatic breast cancer (MBC) are major health issues worldwide as they account for the highest number of cancer-related deaths among women[1]. Early detection of metastasis has been shown to improve the survival rate among BC patients[2], while better stratification of patients into good and poor-prognosis groups would lead to a more personalized medicine approach. Although research was conducted on biomarkers for these purposes, the identified markers were confined to specific types of MBC and lacked sensitivity and specificity[3-5]. Therefore, there is an urgent need for predictive or prognostic biomarkers that can improve the quality of life for these patients. Circulating tumor cells (CTC) have emerged as promising prognostic biomarker in MBC, in general, and has been approved by the FDA, although limitations regarding its enrichment and detection methods are debated[6]. However, currently, the prognosis and risk assessment is largely achieved by clinco-pathological features such as age of diagnosis, tumor size, number and types of sites of metastasis, receptor status, distant disease-free survival (DDFS), etc.[7-9]. Nevertheless, there are no markers for early detection of metastasis which could indicate disease spread before being clinically discernible through imaging techniques. Thus, there exists a lacuna in the area of biomarkers for predicting prognosis across all types of MBC and early detection of metastasis in BC. Since their discovery in placenta, circulating miRNAs, which represent the miRNA population in cell-free portion of blood and body fluids, have attracted tremendous interest in the field of biomarker discovery[10]. Features such as high stability, access by minimally-invasive methods and possibility of repeated sampling make them ideal candidates for use as biomarkers[11]. As described before, for several types of cancer, in particular BC non-invasive techniques for the early detection are still missing. In addition, it would be highly desirable to have means for determining the susceptibility and risk evaluation for a subject to develop those cancers and to provide a non-invasive, highly efficient, easy, reliable, and low cost method for the early detection of BC, as well as other cancers.

This technical problem has been solved by the embodiments as characterized in the claims and described further below and illustrated in the Examples showing for the first time the identification of circulating miRNAs that can discriminate patients depending on their CTC status and that could predict prognosis in MBC patients by adopting a global profiling approach, followed by validation in two independent cohorts.

SUMMARY OF THE INVENTION

The present invention generally relates to a non-invasive method for the prediction of the onset of metastasis in a primary breast cancer patient or the progression-free survival (PFS) or overall survival (OS) of a patient with metastatic breast cancer. As shown in the Examples, the present invention is based on the observation of a global profiling of circulating miRNAs from MBC patients that show a correlation between the presence, absence, or altered level of miRNAs and the risk of developing breast cancer (BC) and in particular metastatic breast cancer (MBC).

In particular, the present invention relates to a non-invasive method for the prediction of the onset of metastasis in a primary breast cancer patient or the progression-free survival (PFS) or overall survival (OS) of a patient with metastatic breast cancer. This method comprise the providing of a biological sample from a primary breast cancer patient or a patient with metastatic breast cancer and determining the presence of at least one miRNA. The presence, absence or altered level of the at least one miRNA is then compared to a corresponding reference value or control sample which is indicative for the risk of the onset of metastasis in a primary breast cancer patient and PFS or OS of a patient with metastatic breast cancer, respectively.

In one embodiment, the miRNA is selected from the group consisting of miR-22, miR-141, miR-144, miR-149, miR-193b, miR-200a, miR-200b, miR-200c, miR-203, miR-215, miR-365, miR-375, mi-429, miR-486-5p, miR-770-5p, miR-1260, miR-1274a or any combination thereof.

In a further embodiment, the determination of miR-141, miR-144, miR-193b, miR-200a, miR-200b, miR-200c, miR-203, miR-210, miR-215, miR-365, miR-375, miR-429, miR-486-5p, miR-801, miR-1274a, miR-1260, and miR-1274a or any combination thereof is characteristic for the overall survival (OS) of a patient with metastatic breast cancer. In a preferred embodiment, the determination of miR-141, miR-144, miR-193b, miR-200a, miR-200b, miR-200c, miR-203, miR-215, miR-375, miR-429, miR-1260 and miR-1274a or any combination thereof is characteristic for prediction of the progression-free survival (PFS) of a patient with metastatic breast cancer.

In another embodiment of the present invention, the determination of miR-200a, miR-200b, miR-200c, miR-210, miR-215 and/or miR-486-5p is characteristic for prediction of the onset of metastasis in a primary breast cancer patient.

In one embodiment of the present invention, the biological sample is peripheral blood or derivative thereof. In a preferred embodiment the biological sample is plasma.

In another embodiment of the present invention, the metastatic breast cancer also includes metastasis in visceral and/or non-visceral organs or any combination thereof. In a preferred embodiment the metastatic breast cancer also includes metastasis in the bone, lungs, regional lymph nodes, liver or brain, or any combination thereof.

In one embodiment, the present invention relates to a method for monitoring the therapy of a patient being treated against primary breast cancer or metastatic breast cancer comprising:
  (a) providing a biological sample from said patient and
  (b) predicting the onset of metastasis in a primary breast cancer patient or the progression-free survival (PFS) or overall survival (OS) of a patient with metastatic breast cancer as described above.

Furthermore, in one embodiment a composition is provided comprising at least two miRNAs. In a preferred embodiment the composition comprise miRNAs as defined above. The composition might also be used in the non-invasive method for the prediction of the onset of metastasis in a primary breast cancer patient or the progression-free survival (PFS) or overall survival (OS) of a patient with metastatic breast cancer as described above.

The present invention also relates to anticancer agents for use in the prevention, amelioration or treatment of the onset of metastasis in a primary breast cancer in a patient. The patient is characterised by the presence, absence or altered level of at least one miRNA compared to a corresponding reference value or control sample which is indicative for the risk of the onset of metastasis in a primary breast cancer patient and PFS or OS of a patient with metastatic breast cancer. In a preferred embodiment, the anticancer agent is used in the prevention, amelioration or treatment of the onset of metastasis in a primary breast cancer or the progression-free survival (PFS) or overall survival (OS) in a metastatic breast cancer wherein the onset is predicted according to the method the methods described above. In one embodiment the anticancer is selected from the group consisting of chemotherapeutic drugs, radiotherapy, antibody agents, and/or therapeutic agents targeting hormones.

In one embodiment the present invention relates to a method of dosing the anti-cancer agent for use in the prevention or treatment of metastatic breast cancer. The method comprises the method for the prediction of the onset of metastasis in a primary breast cancer patient, the progression-free survival (PFS) or overall survival (OS) of a patient with metastatic breast cancer, and a preparation of a pharmaceutical composition comprising an effective amount of said anti-cancer agent and/or administration of the pharmaceutical composition with a dosage regime adapted for the prevention, amelioration or treatment of the onset of metastasis in a primary breast cancer.

The present invention also provides a pharmaceutical and diagnostic, respectively, kit for the prediction of the onset of metastasis in a primary breast cancer patient or the progression-free survival (PFS) or overall survival (OS) of a patient with metastatic breast cancer. The kit can comprise instructions for conducting the method for the prediction of the onset of metastasis in a primary breast cancer patient or the progression-free survival (PFS) or overall survival (OS) of a patient with metastatic breast cancer, and a composition and/or an anticancer agent as described above.

In one embodiment the present invention also provides a device for the prediction of the onset of metastasis in a primary breast cancer patient or the progression-free survival (PFS) or overall survival (OS) of a patient with metastatic breast cancer. This device comprise an analysing unit comprising a detection agent for determining the presence of at least one miRNA selected from the group consisting of miR-22, miR-141, miR-144, miR-149, miR-193b, miR-200a, miR-200b, miR-200c, miR-203, miR-215, miR-365, miR-375, mi-429, miR-486-5p, miR-770-5p, miR-1260, miR-1274a or any combination thereof in a biological sample by means of employing the method for the prediction of the onset of metastasis in a primary breast cancer patient or the progression-free survival (PFS) or overall survival (OS) of a patient with metastatic breast cancer.

Furthermore, in one embodiment of the present invention miR-22, miR-141, miR-144, miR-149, miR-193b, miR-200a, miR-200b, miR-200c, miR-203, miR-215, miR-365, miR-375, mi-429, miR-486-5p, miR-770-5p, miR-1260, miR-1274a or any combination thereof are used for the prediction of the onset of metastasis in a primary breast cancer patient or the progression-free survival (PFS) or overall survival (OS) of a patient with metastatic breast cancer. Further embodiments of the present invention will be apparent from the description and Examples below.

The foregoing description of related art is not intended in any way as an admission that any of the documents described therein are prior art to embodiments of the present invention. Each of the publications cited therein, e.g., journal articles, patent applications and GENEBANK Accession numbers, is incorporated by reference herein.

BRIEF DESCRIPTION OF THE DRAWINGS

FIG. 1A shows clustering of samples with poor (red) and good prognosis (green) using top 15 miRNAs hits from limma analysis, and FIG. 1B shows clustering of patients who are dead (red) and those who are alive (green) using top 86 miRNAs hits from limma analysis.

FIG. 6A and FIG. 6B show IPEC in MBCBL samples, and FIG. 6C and FIG. 6D show MBC1C samples.

FIG. 8 shows clinical distribution of MBCBL patients from cohort I used for miRNA profiling by TLDA. Histology and receptor status refers to those of primary tumor of the patient.

FIGS. 9A-B show distribution of clinical features of Cohort I patients, $MBC_{BL}$ (n=234) and $MBC_{1C}$ (n=119) samples. Therapy data refers to those administered to patients before recruitment into study. The symbol "a" refers to data regarding primary tumor. Abbreviations—: DDFS—distant disease-free survival, ER—estrogen receptor, PR—progesterone receptor, HER2—human epidermal growth factor 2, PFS—progression-free survival.

FIG. 10 shows results of limma analysis of the candidate miRNAs chosen for validation with P<0.05, fold change (FC)>2 or <0.5, and mean Ct<32 for at least one of the group in the comparison.

FIG. 11 shows results of logrank test between miRNA levels or CTC status and survival time, represented by HR, 95% CI, and P-values in $MBC_{BL}$ and $MBC_{1C}$ samples. Samples dichotomized as lower quartile (miRNA high) and upper rest (miRNA low) based on their miRNA Cp values, or as CTC-positive and CTC-negative based on their CTC status. HR calculated as ratio of probability of progression or death of miRNA high/CTC-positive group to that of miRNA low/CTC-negative group. HR greater than 1 denotes that increase in variable decreases probability of survival, while those less than 1 denote that decrease in variable decreases probability of survival.

FIG. 12 shows results of paired Wilcoxon rank sum test comparing miRNA levels at baseline and 1 cycle of therapy. Fold changes (FC)=$2^{-\Delta Cp}$, wherein $\Delta Cp$ corresponds to $MBC_{BL}$-$MBC_{1C}$.

FIG. 13 shows different models built with ten-fold cross-validated multivariate LASSO cox regression analysis for PFS and OS in MBCBL and $MBC_{1C}$ samples, and the corresponding IPE values.

FIG. 14 shows results of independent validation. HR with 95% CI and P-values from logrank test representing the correlation of miRNAs to OS are given. HR calculated as ratio of probability of progression or death of miRNA high group to that of miRNA low group. FC between M0 patients who developed metastasis to those M0 patients who did not develop metastasis along with their P values is represented under "Metastatic onset".

FIGS. 15A-B show correlation of miRNA to progression-free survival (PFS) or overall survival (OS). FIG. 15A shows correlation of miRNA to PFS or OS in Cohort I samples at baseline. FIG. 15B shows correlation of miRNA to PFS or OS in Cohort I samples after therapy.

FIG. 16A shows the comparison of the miRNA model prediction error to that of prognostic markers for MBC, circulating tumor cell status (CTC) at baseline and after therapy. FIG. 16B shows the correlation of miRNA to onset of metastasis in Cohort II.

DETAILED DESCRIPTION OF THE INVENTION

Prognostic biomarkers that divulge information regarding the spread of disease to distant sites, progression of disease, survival of patients have important clinical applications. They help oncologists in decision-making processes and to adopt appropriate treatment regime for the patients[8]. Blood-based biomarkers have advantages over tissue markers as they can be accessed easily and can also be routinely monitored.

However, prognosis and risk assessment are largely achieved by clincio-pathological features such as age of diagnosis, tumor size, number and types of sites of metastasis, receptor status, distant disease-free survival (DDFS), etc[7-9]. Moreover there are no markers for early detection of metastasis which could indicate disease spread before being clinically discernible through imaging techniques.

The present invention generally relates to a method for early prediction of the onset of metastasis and, as shown in the Examples is based on experiments performed in accordance with the present invention revealing that blood-based biomarkers, i.e. circulating miRNAs, could be associated with onset of metastasis, in particular in a primary breast cancer patient. Furthermore, it could be shown that circulating miRNAs are capable of prediction of the progression-free survival (PFS) or the overall survival (OS) of a patient with metastatic breast cancer (MBC). Therefore, the present invention provides miRNA as well as their profile signatures which could serve as marker for the prediction of the onset of metastasis. More specifically, the present invention relates to a non-invasive method for the prediction of the onset of metastasis in a primary breast cancer patient or the progression-free survival (PFS) or overall survival (OS) of a patient with metastatic breast cancer, comprising:
  (a) providing a biological sample from a primary breast cancer patient or a patient with metastatic breast cancer; and
  (b) determining the presence of at least one miRNA;
    wherein the presence, absence or altered level of the at least one miRNA compared to a corresponding reference value or control sample is indicative for the risk of the onset of metastasis in a primary breast cancer patient and PFS or OS of a patient with metastatic breast cancer, respectively.

MicroRNAs (miRNAs) has been discovered in both plant and animal genomes as a class of evolutionarily conserved small single-stranded noncoding RNAs. It was shown by several studies that plasma miRNAs are remarkably stable, for review see e.g. Creemers et al, Circ Res. 110 (2012), 483-495. Because of their stability in plasma and circulation as well as and the ease by which miRNAs can be detected in a quantitative manner by methods such as real-time PCR and microarrays, circulating miRNAs may be used as clinical biomarkers.

Figure 1A:
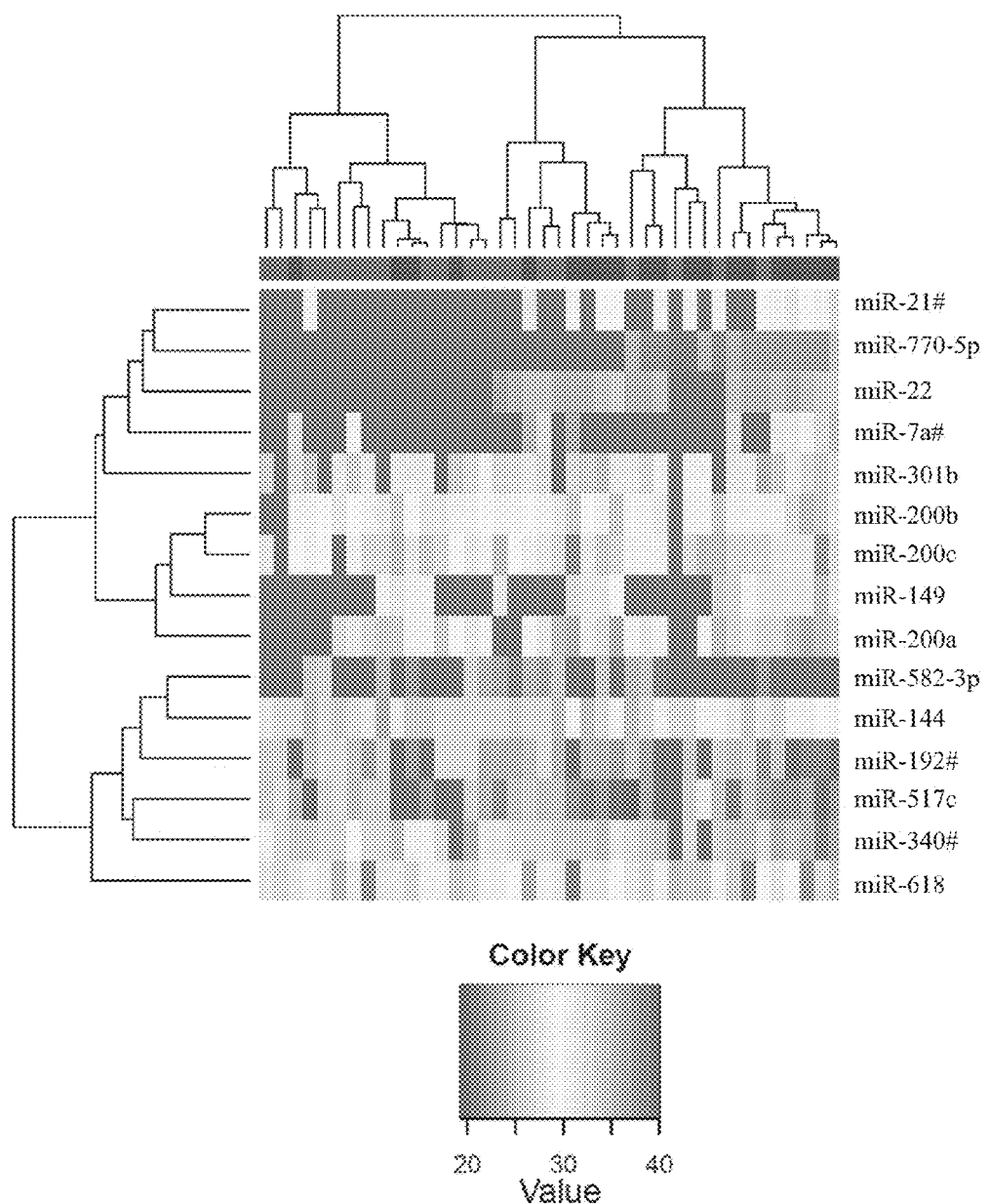
FIGS. 1A-B show Pearson clustering of samples based on miRNAs with P<0.01 for the corresponding limma analysis.
Figure 1B:
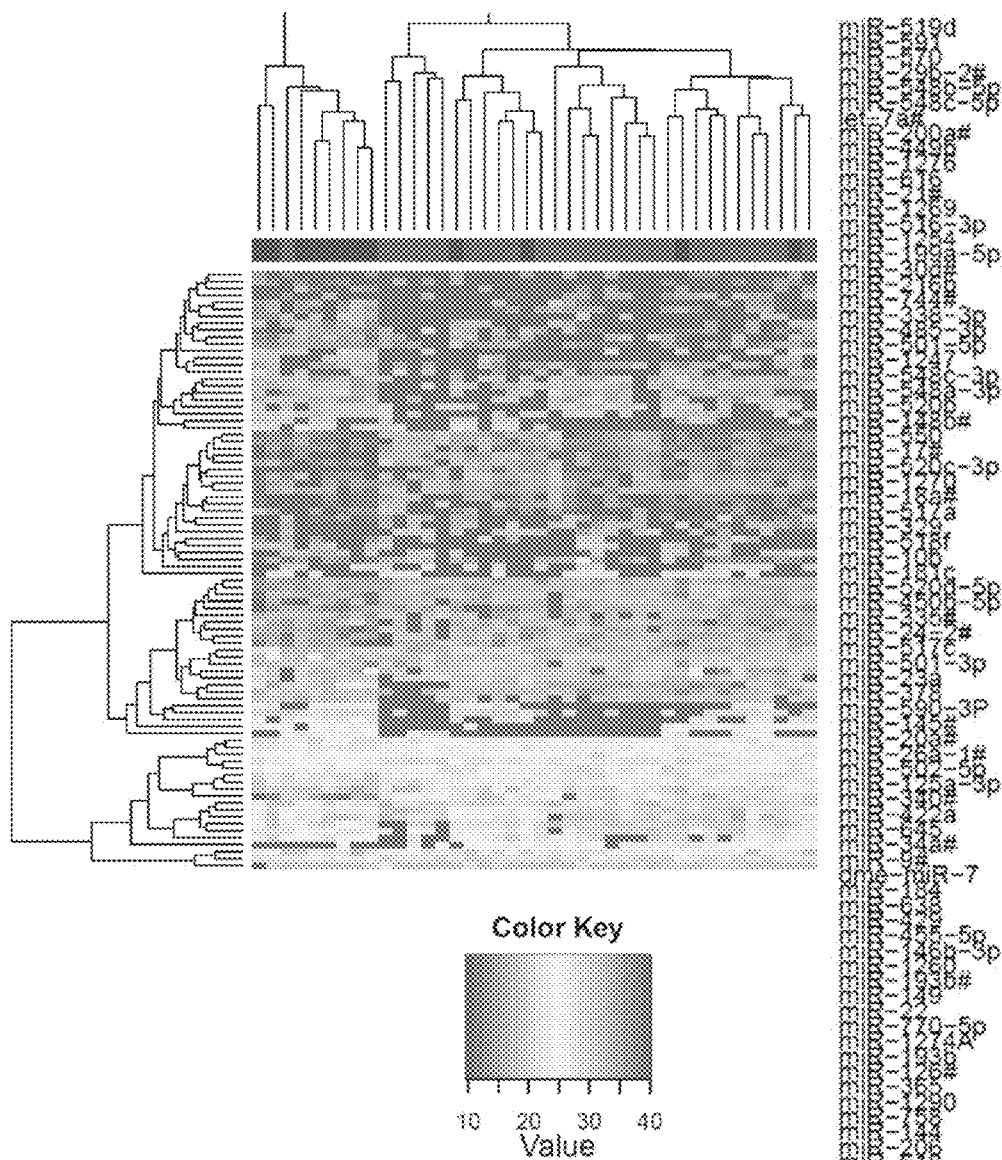
Figure 2A:
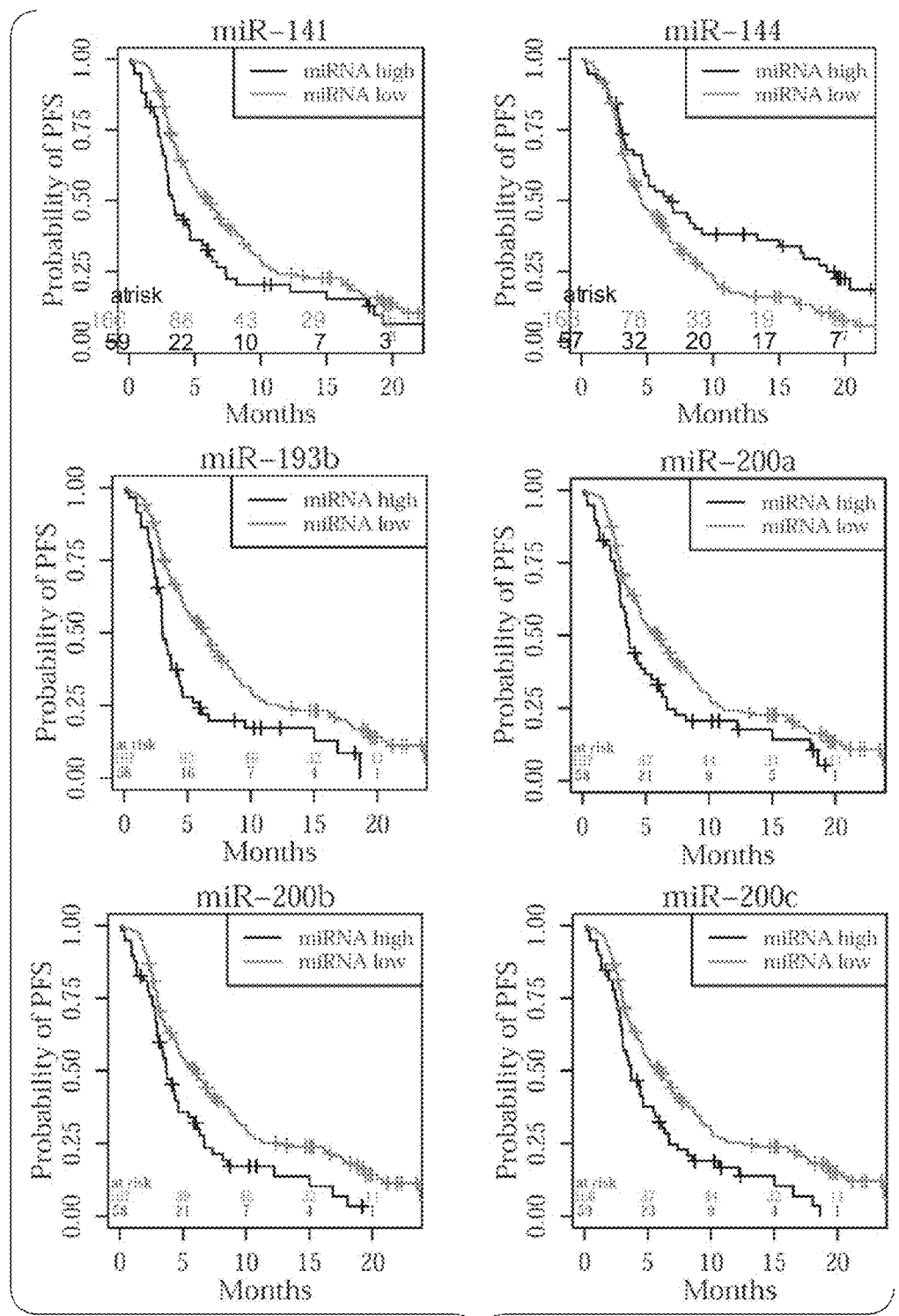
FIGS. 2A-B show Kaplan-Meier curves of miRNAs significantly correlated to PFS in MBC baseline ($MBC_{BL}$) samples and also for CTC status. Samples dichotomized as lower quartile and upper rest based on their miRNA levels or as CTC-positive and CTC-negative based on their CTC status. Number of individuals at risk in each stratum at different time points is indicated along the x-axis.
Figure 2B:
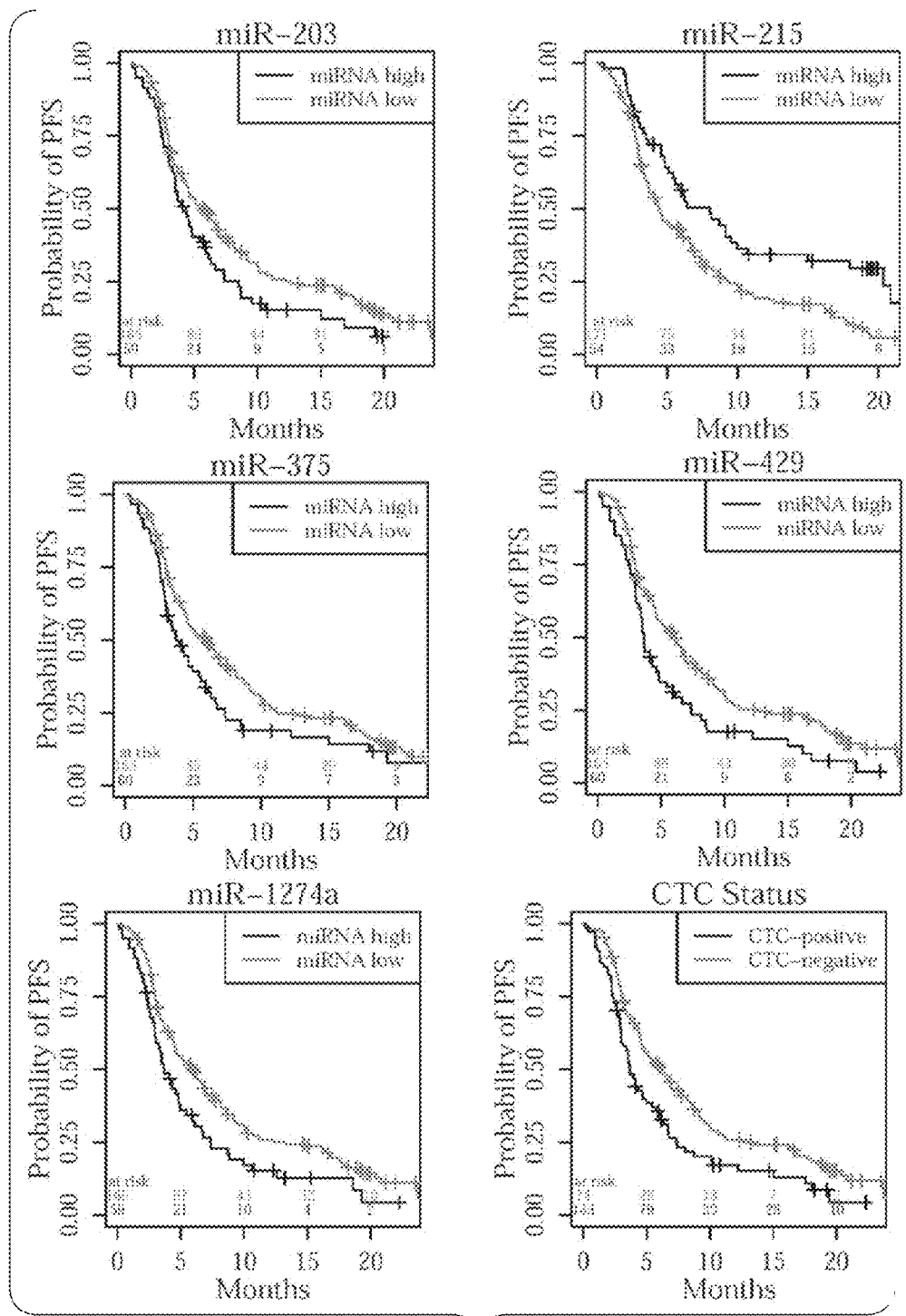
Figure 2C:
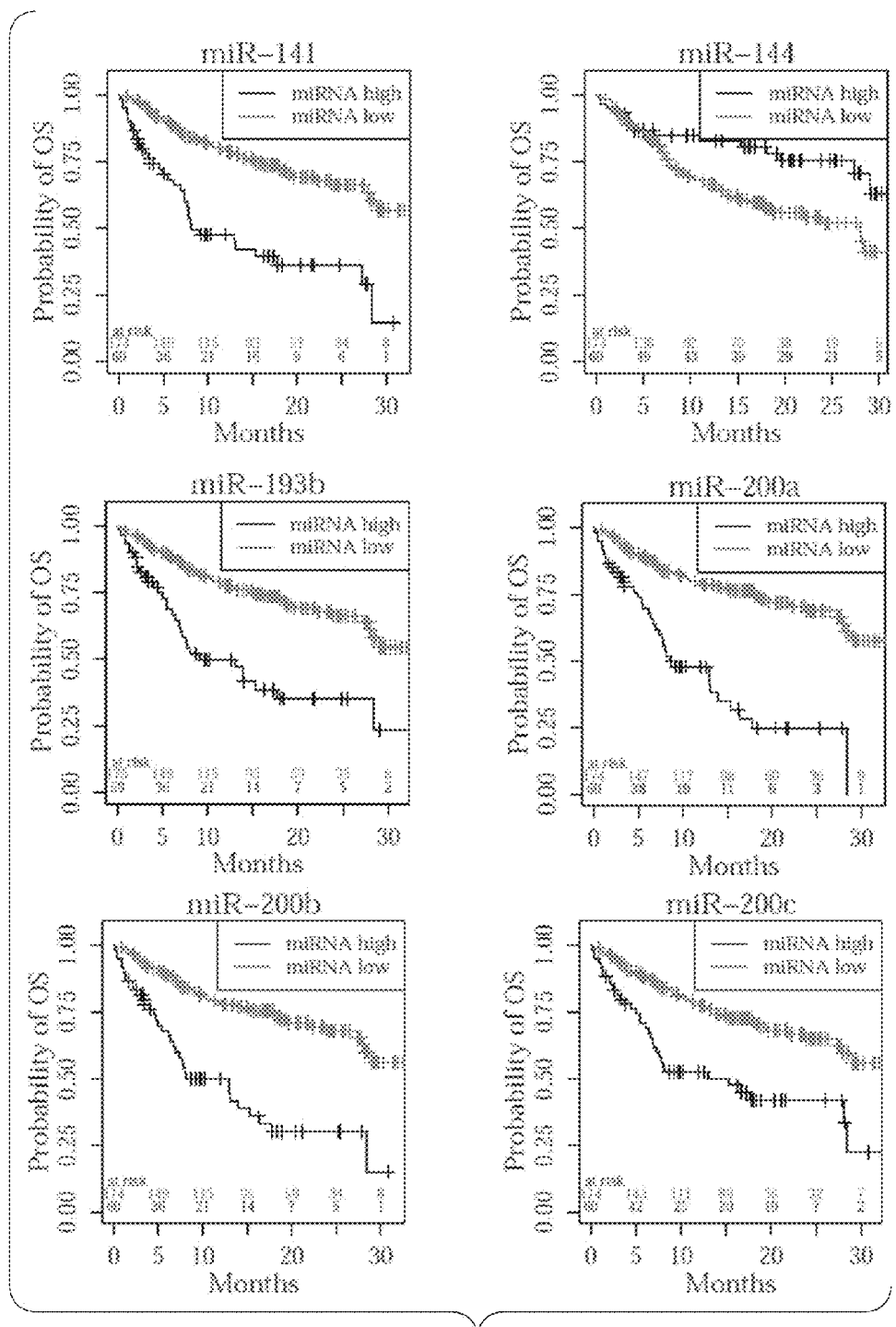
FIGS. 2C-D and FIG. 2E show Kaplan-Meier curves of miRNAs significantly correlated to OS in $MBC_{BL}$ samples and also for CTC status. Samples dichotomized as lower quartile and upper rest based on their miRNA levels or as CTC-positive and CTC-negative based on their CTC status. Number of individuals at risk in each stratum at different time points is indicated along the x-axis.
Figure 2D:
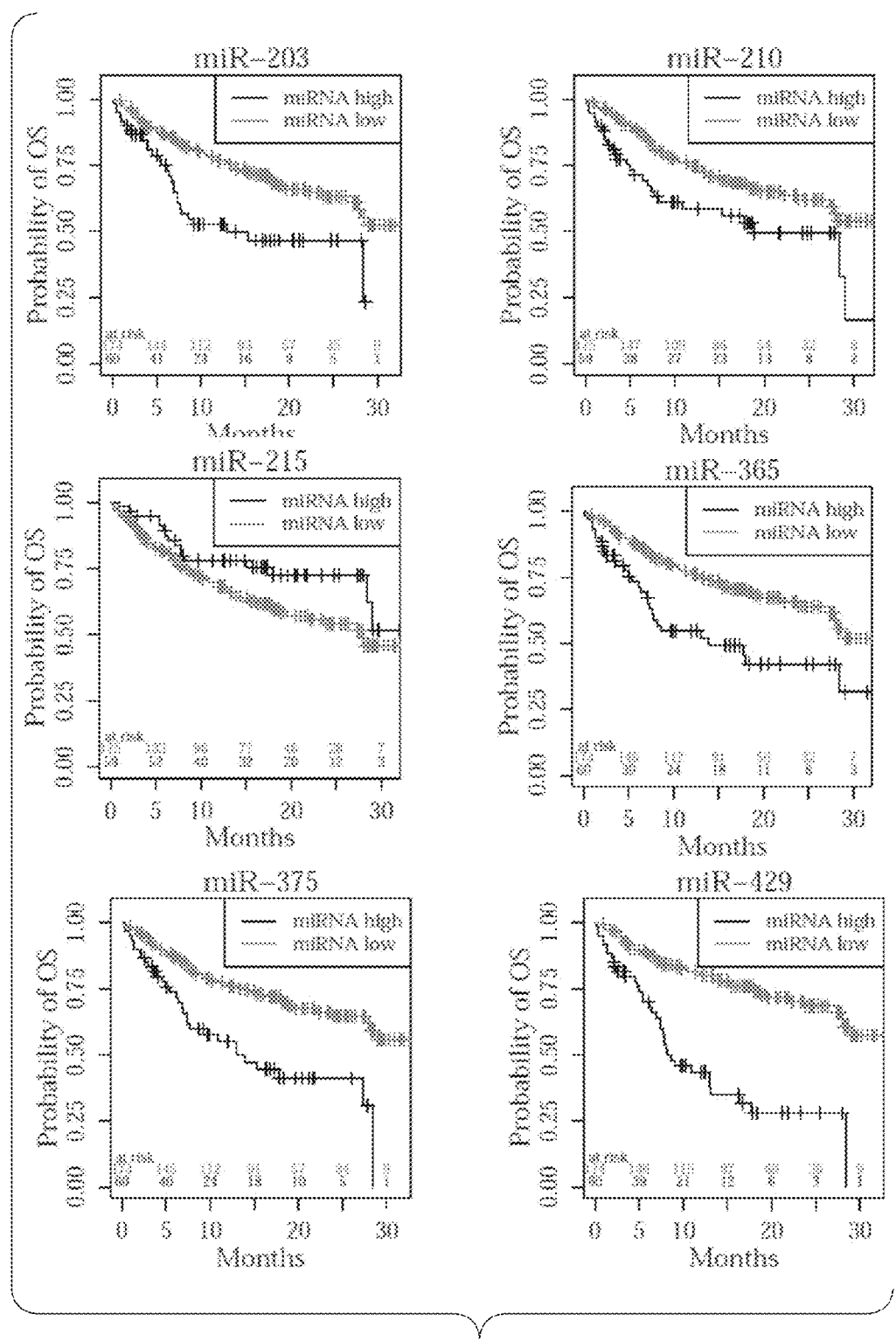
Figure 2E:
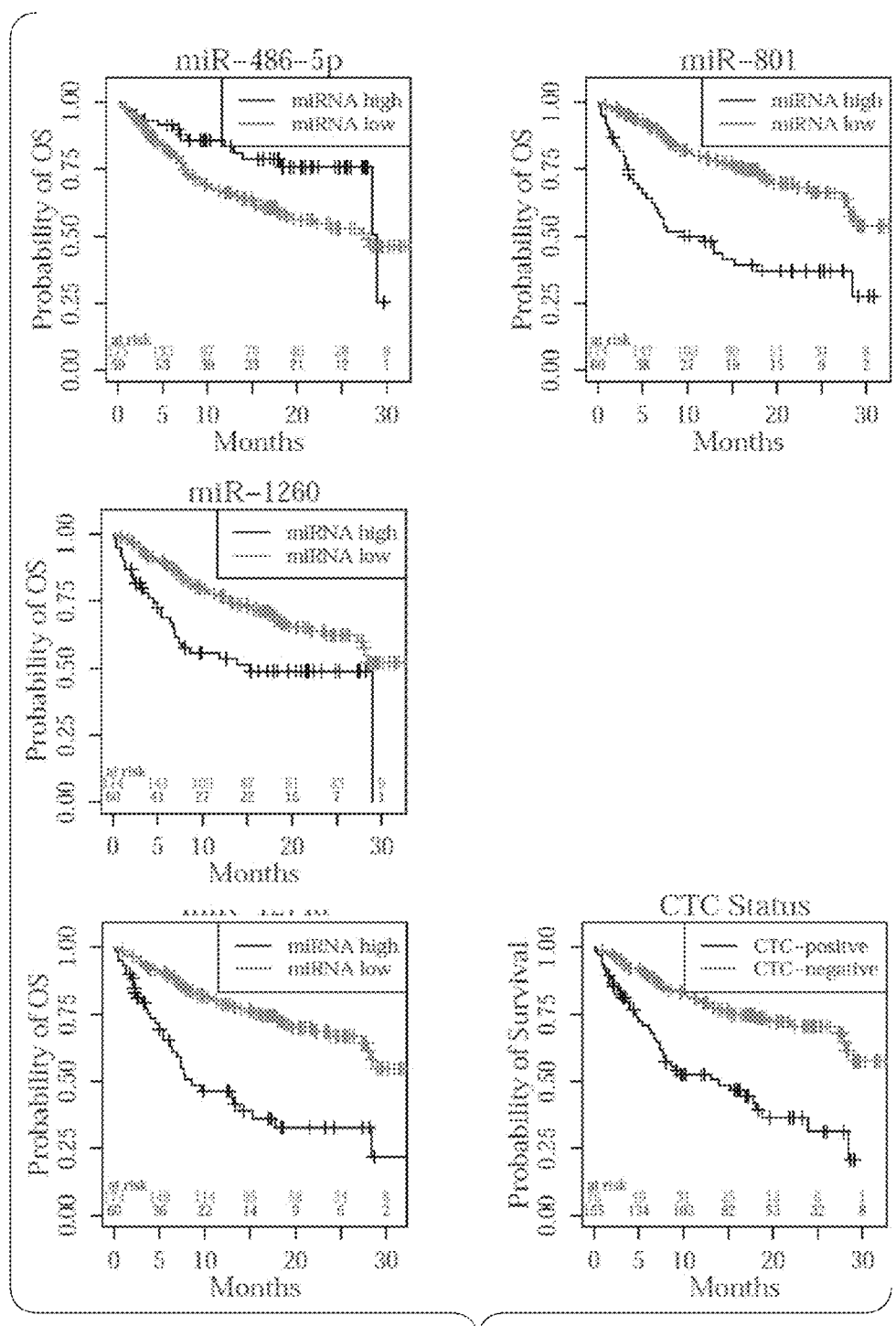

As illustrated in the appended Examples, the method of the present invention at first place is based on observations on global profiling approaches followed by validation of the results in cohorts showing one or more sites of metastasis (cohort I) and/or no metastasis and patients with metastasis from the population-based case control Mamma Carcinoma Risk factor Investigation (MARIE) identifying miRNAs that could predict prognosis in cancer patients. In particular, which could predict prognosis in patients suffering from metastatic breast cancer (MBC). Global profiling of circulating miRNAs from $MBC_{BL}$ samples and Limma analysis, as shown in the Examples, revealed 8 miRNAs significant for the poor vs. bad prognosis and 21 miRNAs showing a significant value between the dead-alive comparison (FIG. 1 and FIG. 10, Example 1). Therefore, in one embodiment of the present invention the presence, absence or altered level of the at least one miRNA selected from the group consisting of miR-22, miR-141, miR-144, miR-149, miR-193b, miR-200a, miR-200b, miR-200c, miR-203, miR-215, miR-365, miR-375, mi-429, miR-486-5p, miR-770-5p, miR-1260, miR-1274a.

Since multiple marker panels are more informative than single miRNAs[26], panels of miRNAs possessing highest accuracy and least redundancy constructed as shown in the Examples. Therefore, in a preferred embodiment of the present invention the presence, absence or altered level of any combination of the miRNA selected from the group consisting of miR-144, miR-193b, miR-215, miR-365, miR-429, miR-486-5p, miR-1260, miR-1274a is determined, which could predict the prognosis for the risk of the onset of metastasis in a primary breast cancer patient and PFS or OS of a patient with metastatic breast cancer, respectively.

Since the progression-free survival (PFS) and the overall survival (OS) are closely related it has been tested whether miRNAs of prognostic value could be validated utilizing the validation method of the present invention, see Examples, to identify miRNAs that would be capable of predicting PFS and OS.

The analysis revealed that miR-141, miR-144, miR-193b, miR-200a, miR-200b, miR-200c, miR-203, miR-215, miR-375, miR-429, miR-1274a, miR-210, miR-365, miR-486-5p, miR-801, and miR-1274a correlated to OS in MBC patients and is characteristic for OS (FIG. 11). Therefore, in one embodiment of the present invention the expression of miR-141, miR-144, miR-193b, miR-200a, miR-200b, miR-200c, miR-203, miR-210, miR-215, miR-365, miR-375, miR-429, miR-486-5p, miR-801, miR-1260, and miR-1274a or any combination thereof is determined for use in the characterization for the overall survival (OS) of a patient with metastatic breast cancer.

Additionally, plasma levels of miR-141, miR-144, miR-193b, miR-200a, miR-200b, miR-200c, miR-203, miR-215, miR-375, miR-429, and miR-1274a has been identified which are significantly associated to PFS (FIG. 11). Accordingly, in one embodiment the method performed in accordance with the present invention comprises the determination of miR-141, miR-144, miR-193b, miR-200a, miR-200b, miR-200c, miR-203, miR-215, miR-375, miR-429, and miR-1274a or any combination thereof, wherein the presence, absence or altered level of the at least one miRNA is characteristic for the prediction of the progression-free survival (PFS) of a patient with metastatic breast cancer.

Interestingly, it was assessed that the majority of the miRNAs remained significantly correlated to PFS and OS even after one cycle of therapy. This is important, since prognosis of a patient is dynamic and should change depending on their response to therapy, and the biomarker one has identified should reflect the true current prognostic status of the patient.

As shown in Example 6 and FIG. 14 the miRNAs miR-200a, miR-200b, miR-200c, miR-210, miR-215 and miR-486-5p were capable of predicting distant disease-free survival (DDFS) and therefore demonstrates their use as early detection markers of metastasis, which can predict disease spread even two years before clinical diagnosis of metastasis. In view of the results shown in the Figures and Examples, in one embodiment of the present invention the method is used for the prediction of the onset of metastasis in a primary breast cancer patient. In particular, the prediction of the onset of metastasis in a primary breast cancer patient is performed determining the miR-200a, miR-200b, miR-200c, miR-210, miR-215, and/or miR-486-5p which have been shown to be characteristic for the onset of metastasis (FIG. 14).

The terms "biological sample", "sample", and "clinical sample" are used interchangeable herein and include but are not limited to, tissue biopsy, autopsy material, pathology specimens, sections of tissues, cells, body fluids, such as blood, sputum, serum, milk, saliva, or urine, or fractions and/or components thereof. As illustrated in the Examples blood samples have been used which provides the advantage of easy collection of the samples and the possibility to take recourse of blood samples collected previously for other diagnostic purposes. Therefore, in a preferred embodiment the sample from the subject to be analyzed in accordance with the method of the present invention is a body fluid, preferably peripheral blood or derived thereof. In a particularly preferred embodiment the sample is plasma, see also the Examples.

A "control", "control sample", or "reference value" terms which are used interchangeable herein, are to be understand as a sample or standard used for comparison with the experimental sample. The control may include a sample obtained from a healthy subject without cancer or a non-tumor sample. Additionally a control may also be a standard reference value or range of values, i.e. such as stable expressed miRNAs in the samples, for example the endogenous control cel-miR-39. However, as shown in the Examples values determined in accordance with the present invention may also be used as control or reference value. In particular, for the first time two endogenous controls, have been identified, which showed high stability across the MBC plasma samples. As shown in Example 1, the two identified miRNAs which were found to be the most stably expressed miRNAs and were therefore used it to normalize the validation data, were miR-29a and miR-139-5p. Thus, in one embodiment of the present invention, miR-29a and miR-139-5p are used as endogenous controls to normalize the validation data.

In this context, it is understood that for the purpose of the method of the present invention the term "control" also include embodiments where a sample from a subject previously determined to suffer from or be at risk of developing cancer may be the source of a control sample irrespective whether or not the subject has been diagnosed with a method of the present invention or an equivalent diagnostic tool. Similarly, the term "reference value" includes embodiments where the standard reference value or range of values has been determined to be indicative for the onset developing cancer, in particular breast cancer (BC), onset of metastasis, overall survival (OS), and/or progression-free survival (PFS), and thus may serve as a "positive" without the need for a control or reference value obtained from a healthy volunteer. Accordingly, in one embodiment, the values determined in accordance with the method of the present invention for subjects afflicted with cancer depicted in any one of the FIGS. 11-15 may generally serve as reference values.

The metastasis may also spread from breast to other distant organs. The most common sites of metastasis in further organs is shown in FIG. 9. Therefore, in another embodiment of the present invention the metastatic breast cancer can also include metastasis of other distant organs, in particular metastasis in visceral and non-visceral organs. In a preferred embodiment the metastasis is in the bone, lungs, regional lymph nodes, liver or brain or any combination thereof.

In one embodiment of the present invention, a composition comprising at least two miRNAs as defined supra is designed. In addition such a composition may comprise suitable means for detection such as reagents conventionally used in immuno- or nucleic acid-based diagnostic methods. In a preferred embodiment the composition is used in the non-invasive method as described above for the prediction of the onset of metastasis in a primary breast cancer patient or the progression-free survival (PFS) or overall survival (OS) of a patient with metastatic breast cancer.

In addition to the ability to as early detectors and/or predictors of metastasis, the presence, absence or altered level of the at least one miRNA as described above compared to a corresponding reference value or control, may be used for monitoring the therapy of a patient being treated against primary breast cancer or metastatic breast cancer. As shown in the Examples and explanations herein, the determination and/or discrimination of the prognosis of a patient by determining the expression level is possible. Therefore, in one embodiment the present invention also relates to a method for monitoring the therapy of a subject being treated against primary breast cancer or metastatic breast cancer. In particular, the method comprises the steps of providing a sample from the subject and predicting and determining the onset of metastasis in a primary breast cancer patient or the progression-free survival (PFS) or overall survival (OS) of a patient with metastatic breast cancer as described above. In a preferred embodiment, the sample utilized in the method for monitoring of therapy is peripheral blood, in a particular preferred embodiment plasma. In addition, the altered miRNA expression profile compared to a reference sample, obtained e.g. from the subject before or at an earlier stage of the treatment indicate the effectiveness of a treatment course undergoing the subject.

In addition, due to the possibility of the early detection and prediction of cancer, in particular metastatic breast cancer, a treatment regimen can be developed. In view of the probability and/or the determined prognosis, e.g. good vs. bad, one or more candidate genes can be utilized as biomarkers for the early prediction of cancer as shown by the Examples and explanations above. Additionally, cancer treatment can be envisaged in view of the altered miRNA expression of the present invention. This is particular advantageous since a treatment corresponding to the prognosis, i.e. miRNA expression, may be performed. A further advantage is the more precise treatment which may be possible due to the severity, i.e. prognosis. In particular, side effects of cancer treatment, dependent on the severity of the cancer and treatment such as typical side effects of chemotherapy might be avoided.

In this context, in one embodiment the method of the present invention includes the provision an appropriate therapy for the subject affected or at risk developing cancer. In some embodiments, the therapy includes the administration of an anticancer agent for use in the treatment, prevention or amelioration of the onset of metastasis in a primary breast cancer in a patient, wherein said patient is characterized by the presence, absence or altered level of at least one miRNA. In a preferred embodiment, the level of miRNA is compared to a corresponding reference value or control sample which is indicative for the risk of the onset of metastasis. The patient who obtains a treatment with the anticancer agent and has the risk of the onset of metastasis is preferably a patient who has the risk of the onset of metastasis in a primary breast cancer patient and PFS or OS of a patient with metastatic breast cancer.

As already mentioned above, an advantage of the present invention is that method enables the identification of the onset of metastasis. For this reason, the treatment with the anticancer agent for preventing, ameliorating, or treating of the onset of metastasis in a subject can occur at an early stage of cancer. Therefore, the treatment might also serve as a kind of prevention to avoid the onset of metastasis or symptoms thereof. The anticancer agent can be administered to the subject at a suitable dose and can be effected by different ways, e.g. by intravenous, intraperitoneal, subcutaneous, intramuscular, intranasal, topical or intradermal administration or spinal or brain delivery, but also in aerosolic formulations and formulations for rectal or vaginal administration with a suitable carrier.

The dosage will be determined by the attending physician and clinical factors but can also be adjusted in accordance with the diagnosis as set forth above or the progression or regression of the onset of metastasis which is to be assessed e.g. by the method for the prediction of the onset of metastasis as described above. Accordingly, in one embodiment the present invention relates to a method of dosing the anti-cancer agent for use in the prevention or treatment of metastatic breast cancer, comprising (a) for the prediction of the onset of metastasis as described above; and (b) preparing a pharmaceutical composition comprising an effective amount of said anticancer agent; and/or (c) administering said pharmaceutical composition with a dosage regime adapted for the prevention, amelioration or treatment of the onset of metastasis in a primary breast cancer.

The anti-cancer agent can be one or more agent selected from the group consisting of, but not limited to chemotherapeutic drugs such as cisplatin, cyclophosphamide, taxanes, bisphosphonate; radiotherapy; antibody agents such as trastuzumab, bevacizumab; therapeutic agents targeting hormones (endocrine therapy) such as tamoxifen, letrozol, exemestan. In one embodiment of the present invention, the anticancer agent might be useful in the amelioration, prevention, or treatment of the onset of metastasis in a primary breast cancer or the progression-free survival (PFS) or overall survival (OS) in a metastatic breast cancer which is predicted according to the method as described above.

The present invention also relates to a kit comprising one or more containers filled with one or more ingredients of the above described method. For example the kit is suitable for the determination of the miRNA expression level in accordance with the present invention. In particular the kit may comprise one or more primer pairs for amplifying at least one miRNA or a fragment and/or for analyzing the product amplified by such primer pair. In a preferred embodiment, the at least one miRNA identified is selected from the group consisting of miR-141, miR-144, miR-149, miR-193b, miR-200a, miR-200b, miR-200c, miR-203, miR-215, miR-365, miR-375, mi-429, miR-486-5p, miR-1260, miR-1274A. Accordingly, in one embodiment of the present invention a kit for the prediction of the onset of metastasis in a primary breast cancer patient or the progression-free survival (PFS) or overall survival (OS) of a patient with metastatic breast cancer is designed.

The kit utilized in accordance with the method of the present invention, will allow the early prediction of the onset of metastasis cancer in a primary breast cancer patient, or the progression-free survival (PFS) or overall survival (OS) of a patient with metastatic breast cancer. In a preferred embodiment, expression of miRNA determined using the above mentioned kit, wherein the presence, absence or altered level of the at least one miRNA compared to a corresponding reference value or control sample is indicative for the risk of the onset of metastasis in a primary breast cancer patient and PFS or OS of a patient with metastatic breast cancer, respectively. In a preferred embodiment, the presence, absence or altered level of the at least one miRNA is measured in peripheral blood, preferably plasma. In addition or alternatively, the kit may further comprise instructions for carrying out said method and optionally standards for a control or reference as well as reagents and/or instructions for use in appropriate diagnostic assays. The results or output obtained by the kit can be provided in a paper output, a display on a screen, a graphical output, audible output. Furthermore, the data output includes but is not limited to numerical values, graphical presentations, quantitative information, qualitative information. Furthermore, information or guidelines for interpreting the data providing a cut-off value or expression level of the at least one miRNA that is indicative for the risk of the onset of metastasis in a primary breast cancer patient, or PFS or OS of a patient with metastatic breast cancer, can be included in the kit. Furthermore, the kit for use in accordance with the method of the present invention may also comprise compositions as well as one or more anticancer agents as described above.

In an additional or as an alternative embodiment, the method of the present invention relates to a device for predicting breast cancer and/or the onset of metastasis in a primary breast cancer patient, or the PFS or OS of a patient with metastatic breast cancer. This device may comprise two units, i.e. an analyzing and an evaluation unit, which might be separated from each other as two independent units or devices or forming one unit. In a preferred embodiment the device is formed from one unit comprising the analyzing and evaluation unit. In one embodiment the analyzing unit comprises a detection agent for determining the presence of at least one miRNA selected from the group consisting of miR-141, miR-144, miR-149, miR-193b, miR-200a, miR-200b, miR-200c, miR-203, miR-215, miR-365, miR-375, mi-429, miR-486-5p, miR-1260, miR-1274a or any combination thereof. In addition, the analyzing unit can comprise a receptacle for a sample of a subject which is suspected to suffer from or being at risk of developing cancer, preferably breast cancer, particularly preferred onset of metastasis in primary breast cancer, which might be e.g. a disposable test strip. The evaluation unit comprises a data processor having tangibly embedded an algorithm for carrying out a comparison of the amount determined by the analyzing unit with a stored reference and which is capable of generating an output file containing a diagnosis established based on the said comparison. In addition or alternatively, the expression level of stably expressed miRNAs may be determined and used for the comparison. In particular, miRNA miR-29a, miRNA-139-5p, and/or cel-miR-39 can be used.

In a further embodiment of the present invention, the miR-141, miR-144, miR-149, miR-193b, miR-200a, miR-200b, miR-200c, miR-203, miR-215, miR-365, miR-375, mi-429, miR-486-5p, miR-1260, miR-1274a or any combination thereof is/are used for the prediction of the onset of metastasis in a primary breast cancer patient or the progression-free survival (PFS) or overall survival (OS) of a patient with metastatic breast cancer.

These and other embodiments are disclosed and encompassed by the description and Examples of the present invention. Further literature concerning any one of the materials, methods, uses, and compounds to be employed in accordance with the present invention may be retrieved from public libraries and databases, using for example electronic devices. For example the public database "Medline" may be utilized, which is hosted by the National Center for Biotechnology Information (NCBI) and/or the National Library of Medicine at the National Institutes of Health (NLM.NIH). Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

Furthermore, the person skilled in the art will understand that any of the features and parameters described in the Examples and shown in the Figures generally relate to the embodiments characterized in the claims and described herein above. In addition, it is to be understood that each of those features and parameters may be used individually and isolated from the examples and/or in combination including any combination with the embodiments cited in the claims and in the preceding description.

EXAMPLES

Material and Methods
Samples and Study Design

Samples used in this study belonged to two study cohorts. Cohort I consisted of 237 patients with radiologically confirmed presence of one or more sites of metastasis, thus diagnosed with MBC at time of blood draw. Tumor progression was routinely monitored approximately every 3 months and response was classified according to the RECIST guidelines[20]. Peripheral blood was collected in EDTA tubes (Sarstedt S-Monovette R, Nümbrecht, Germany) after recruitment into the study (MBCBL samples). Of the 237 patients, additional blood sample was collected from 117 MBC patients after completing one round of therapy (MBC1C samples). Blood was processed within 2 hours of phlebotomy by a two-step centrifugation protocol; 1300 g for 20 min at 10° C. followed by 15500 g for 10 min at 10° C. of the plasma supernatant obtained from first step. Plasma separated this way was snap-frozen and stored at −80° C. Simultaneous to each blood draw CTC status was additionally determined by evaluating CTCs by the CellSearch R system (Veridex, LLC, Raritan, N.J.). Depending on the number of CTCs, patients were designated as CTC-positive (5 CTCs/7.5 ml blood) or CTC-negative (<5 CTCs/ 7.5 ml blood or no detectable CTCs). Samples of cohort II were drawn from the population-based case control MARIE (Mamma Carcinoma Risk factor Investigation), wherein study subjects were of two types; those with no metastasis (M0, n=265) and those with metastasis (M1, n=67) at baseline. Plasma samples were collected from each patient here. Here, blood samples were centrifuged at 3300 g for 10 minutes. Plasma was separated and stored at −80° C. The plasma samples were thawed and a second centrifugation step was applied (12000 g for 10 minutes). 200 ml of supernatant from this step was aliquoted into a 2 ml tube and stored at −80° C. PFS, OS and DDFS were calculated as time, in months, from blood take to progression of disease or last radiologic examination, death or last visit, and development of metastasis or last follow-up time, respectively. All samples were female and of Caucasian origin. The study was performed in accordance with the principles embodied in the Declaration of Helsinki and approved by the Ethical Committee of the University of Heidelberg (Heidelberg, Germany). Written informed consent was obtained from all participants. The study consisted of three phases: (1) discovery phase, (2) validation phase, and (3) second independent validation phase. While samples from study cohort I was used for the first two phases, study cohort II samples were used for the final phase. miRNA was extracted from 400 ml of plasma (cohort I) or 200 ml of plasma (cohort II) using TRIzol R LS (Invitrogen, Life Technologies, Carlsbad, USA) and Qiagen miRNeasy kit (Qiagen, Hilden, Germany), and spiking in 10 fmol of cel-miR-39, as previously described[17].

Global Profiling of Circulating miRNAs From MBCBL Samples

Circulating miRNA from plasma of MBCBL samples was profiled by TaqMan R Human microRNA cards v3.0 (Applied Biosystems, Life Technologies, Foster City, Carlsbad, USA) following the manufacturer's instructions. Briefly, 3 ml of miRNA sample was reverse transcribed by either Megaplex™ RT Primers, Human Pool A or Pool B v3.0 (Applied Biosystems, Life Technologies, Carlsbad, USA). 5 ml of RT product was preamplified with Megaplex™ Pre-Amp Primers, Human Pool A or Pool B v3.0 (Applied Biosystems, Life Technologies, Carlsbad, USA). The final product was used for the quantitative PCR (qPCR) reaction which was carried out in Applied Biosystems 7900HT machine. Ct value of each miRNA was calculated by the SDS v2.2 software using automatic baseline and threshold setting. 20 samples with good prognosis (PFS and OS>16 months) and 20 samples with poor prognosis (PFS or OS<3 months) were profiled and 754 miRNAs measured (FIG. 8). miRNAs not detected or with Ct>35 across all 40 samples were filtered out. The data was then quantile normalized, and an additional filtration step to remove miRNAs with interquartile range (IQR)<1.5 was applied. Normalized miRNAs remaining after these filtration steps were used for further statistical analysis.

Validation of Candidate miRNAs

Candidate miRNAs chosen from the above discovery round were initially validated in an expanded sample set of 237 $MBC_{BL}$ and 117 $MBC_{1C}$ samples from cohort I by individual TaqMan R assays (FIG. 9). This was followed by an independent validation in 332 samples from cohort II. A constant volume input of 2 ml of sample was introduced into the reverse transcription reaction, in which a maximum of 3 miRNAs were multiplexed in a 7.5 ml reaction mixture. 2.3 ml of reverse transcribed product was subjected to qPCR in a 5 ml reaction mixture containing TaqMan R Universal PCR Master Mix, No AmpEraseUNG (Applied Biosystems, Life Technologies, Carlsbad, USA), using Roche LightCycler R 480 (Roche Applied Sciences, Germany) in triplicates. miRNA was normalized to exogenous control, cel-miR-39, and the identified endogenous controls for initial validation in cohort I, while for the subsequent validation in cohort II only cel-miR-39 normalization was performed. When a miRNA was undetected in a sample, it was replaced with the maximum Cp across all samples for that miRNA and used for data analysis.

Statistical Analysis

All statistical analysis was performed in R3.0.1 environment[21]. For analyzing TLDA data, HTqPCR[22] package from Bioconductorv2.13[23] was used. Limma analysis was performed to compare miRNA profile of (1) samples with good and poor prognosis, and (2) samples from patients who died to those who were alive. miRNAs were chosen as candidates for the validation phase if it had P<0.05 and fold change (FC)>2 or <0.5 for one of the above comparison, and mean Ct<32 in one of the analyzed group. Pearson clustering of samples based on their progression or life status was accomplished based on the miRNA levels of those which had P<0.05 in the corresponding limma analysis. Endogenous controls were identified from a set of miRNAs with IQR<1 and mean Ct<30 using NormFinder[24]. In the validation cohort, correlation between miRNA levels and PFS, OS or DDFS was assessed by logrank tests and constructing Kaplan-Meier curves. miRNA models with highest prediction accuracy and least redundancy were built using LASSO Cox models, wherein a LASSO penalty term was used for automatic selection of relevant miRNA variables (with penalty parameter tuning done by 10-fold cross-validation), and allowing only miRNAs that were significant in the univariate analysis to enter the model. In addition to the miRNA models, models with CTC status alone or miRNA along with CTC status were also built. The prognostic value of models was assessed by 0.632+ bootstrap estimates of prediction error curves and summarized as the integrated prediction error (IPE) curve, and the IPE of different models compared. miRNA data was dichotomized as miRNA low levels and miRNA high levels, while CTC status was retained in its binary state (CTC-positive and CTC-negative), and used for the above survival analysis. Comparison of samples was done by Wilcoxon rank sum tests with two-sided P-value, either paired or unpaired depending on the samples being compared.

Example 1: Identification of Circulating miRNAs With Potential Prognostic Value

Profiling of plasma samples from patients with two extreme prognostic outcomes resulted in identification of candidate miRNAs for predicting PFS or OS. After the initial filtering steps to weed out undetected and miRNAs whose levels were invariant across all samples, 199 miRNAs remained which was used for comparisons and clustering. Limma analysis produced 8 miRNAs that were significantly different between cases with good and poor prognosis, whereas 21 miRNAs were significant for the dead-alive comparison. Six miRNAs namely miR-22, miR-144, miR-149, miR-200a, miR-200b, and miR-200c were common hits for both these comparisons. In total 20 miRNAs were chosen for further validation: miR-22, miR-141, miR-144, miR-146b-3p, miR-149, miR-193b, miR-200a, miR-200b, miR-200c, miR-203, miR-215, miR-365, miR-375, miR-429, miR-486-5p, miR-618, miR-758, miR-770-5p, miR-1260, and miR-1274a (FIG. 10). Clustering of samples into poor and good prognosis (Chi Squared test P=0.00016) or into dead and alive patients (Chi Squared test P<0.000001) based on their respective top hits is shown in FIG. 1. Apart from identifying circulating miRNAs with prognostic capabilities, combination of miR-29a and miR-139-5p was found to be the most stably expressed miRNAs by NormFinder with a stability value of 0.004. Thus, a combination of these miRNAs along with exogenously spiked-in cel-miR-39 was used for normalization in the validation rounds Example 2: Sixteen miRNAs Confirmed to be Significantly Correlated to Survival in MBC Patients Candidate miRNAs were first verified in the 40 samples used in the discovery phase by individual TaqMan R assays. miR-146b-3p, miR-149, miR-618, miR-758, and miR-770-5p were found to be present in very low to undetectable levels and hence not tested in further steps. To the list of remaining 15 miRNAs, miR-210 and miR-801 were added as it had already be shown that they are associated with survival in MBC patients in a previous study[17]. In $MBC_{BL}$ samples, there were in total 187 patients with progression (83%) and 38 without progression (17%); 85 patients who had died (36%) and 149 who were still alive (64%). Logrank tests after stratifying samples based on their miRNA levels revealed 12 miRNAs, miR-141, miR-144, miR-193b, miR-200a, miR-200b, miR-200c, miR-203, miR-215, miR-375, miR-429, miR-801, and miR-1274a to be significantly correlated to PFS (P<0.04 for all, FIG. 2). On the other hand, all miRNAs except miR-22 was found to be associated with OS (P<0.05 for all, FIG. 2, and FIG. 10). Thus, 16 out of the 17 candidate miRNAs were confirmed to possess prognostic significance with respect to either PFS and/or OS. CTC status was also found to be a significant predictor of PFS (P=0.006) and OS (P<0.00001) (FIG. 2, 2).

Example 3: Circulating miRNAs Correspond to Survival after One Cycle of Therapy

Figure 3A:
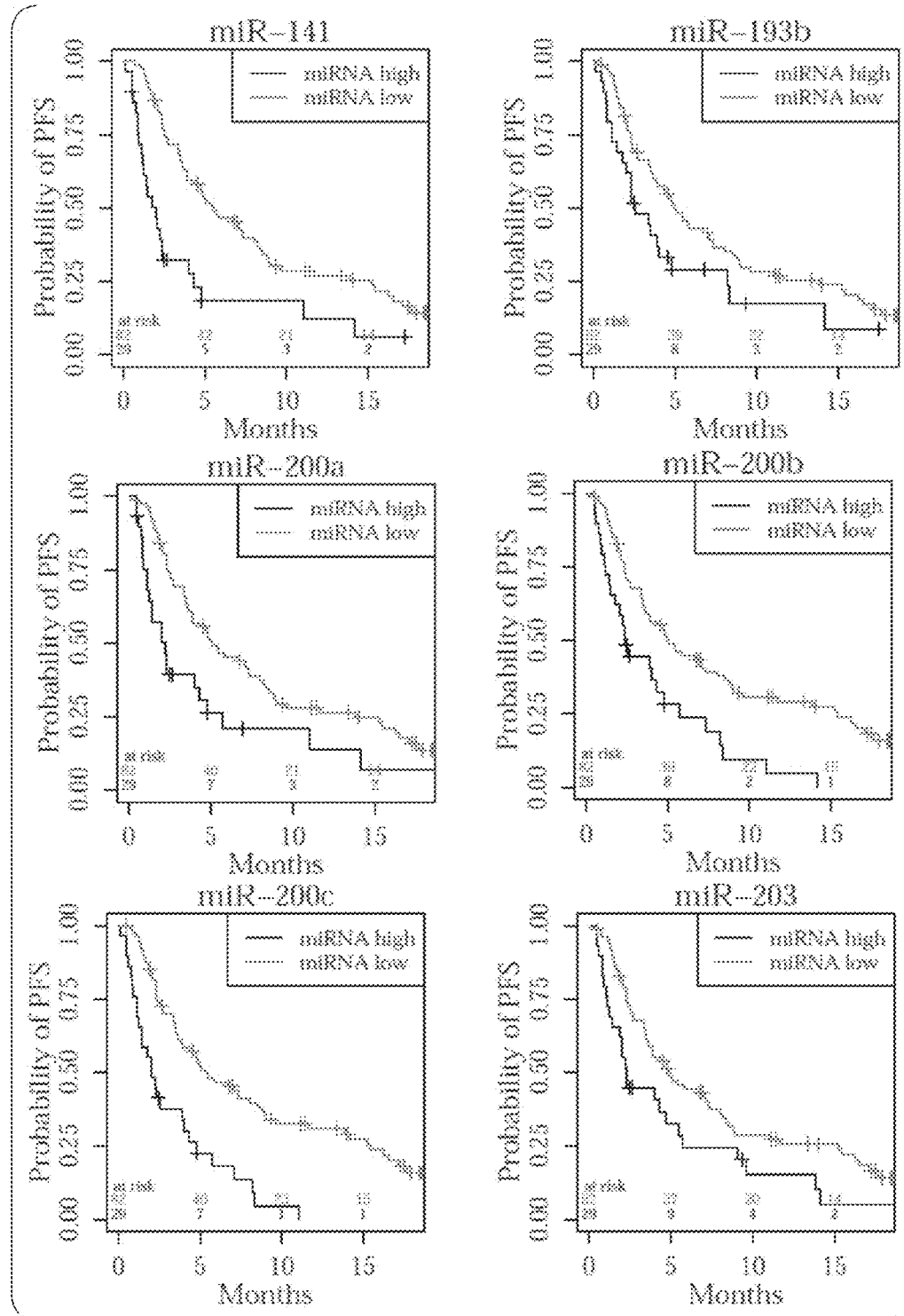
FIGS. 3A-B show Kaplan-Meier curves of miRNAs significantly correlated to PFS in MBC samples after one round of therapy ($MBC_{1C}$) and also for CTC status. Samples dichotomized as lower quartile and upper rest based on their miRNA levels or as CTC-positive and CTC-negative based on their CTC status. Number of individuals at risk in each stratum at different time points is indicated along the x-axis.
Figure 3B:
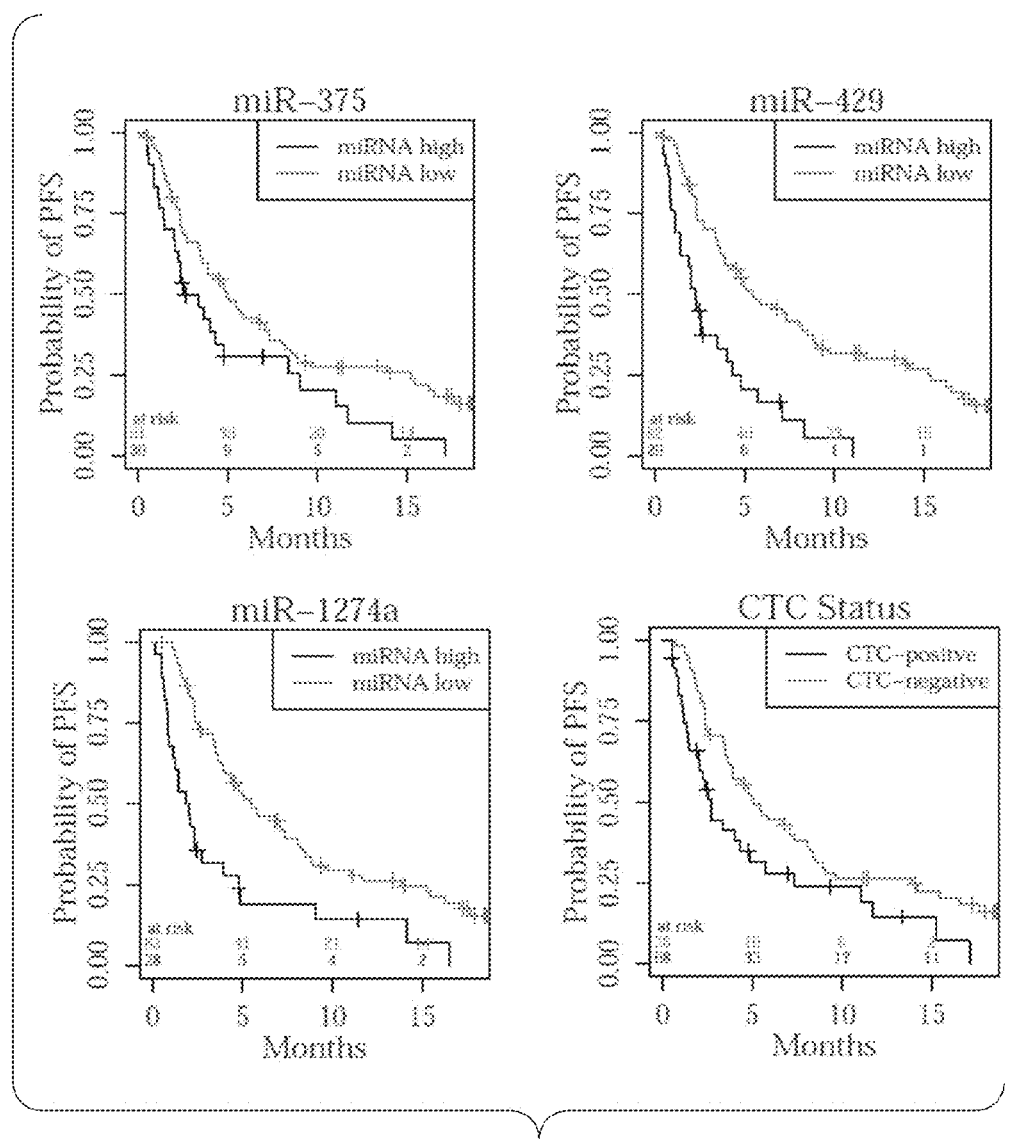
Figure 4A:
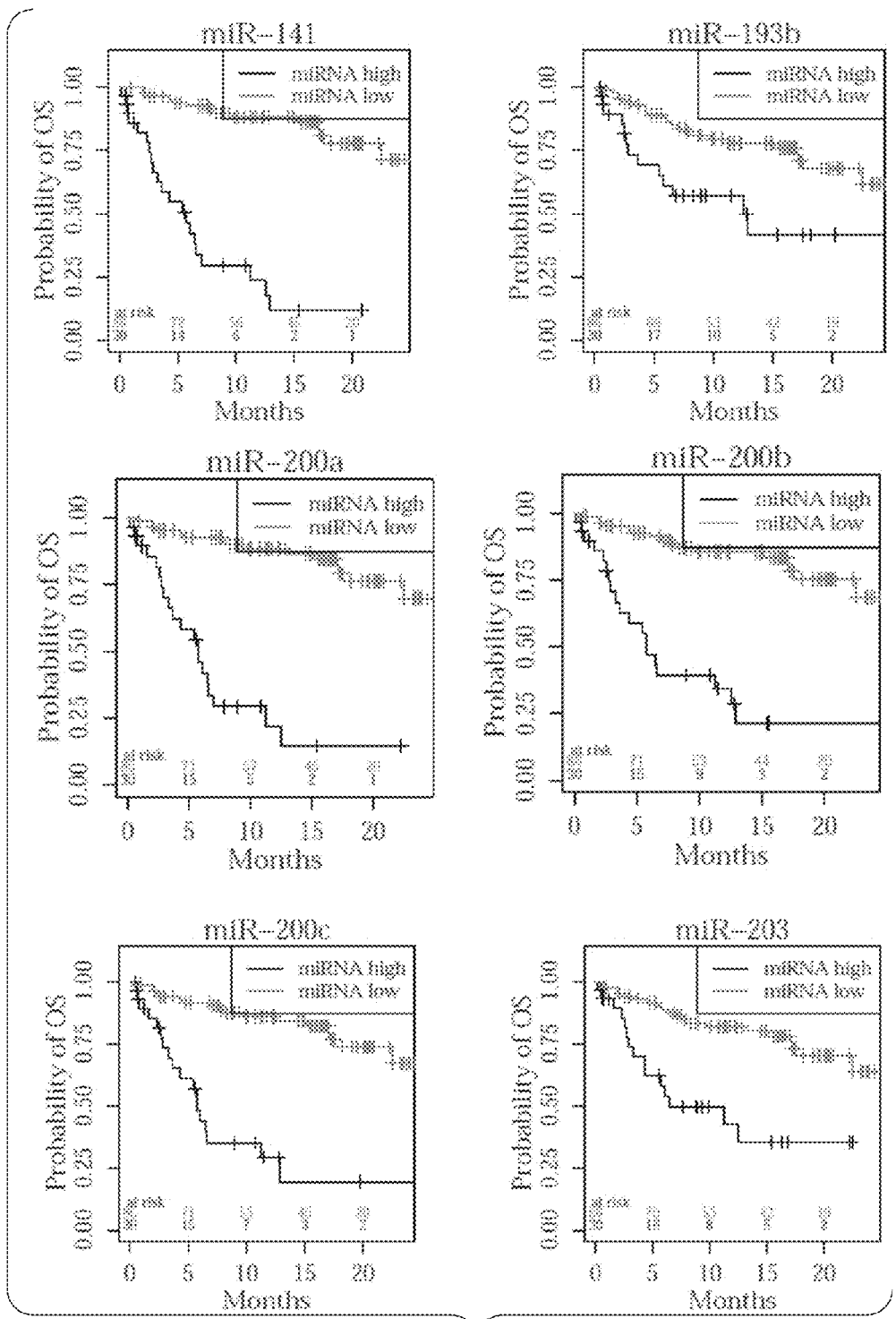
FIGS. 4A-B show Kaplan-Meier curves of miRNAs significantly correlated to OS in $MBC_{1C}$ samples and also for CTC status. Samples dichotomized as lower quartile and upper rest based on their miRNA levels or as CTC-positive and CTC-negative based on their CTC status. Number of individuals at risk in each stratum at different time points is indicated along the x-axis.
Figure 4B:
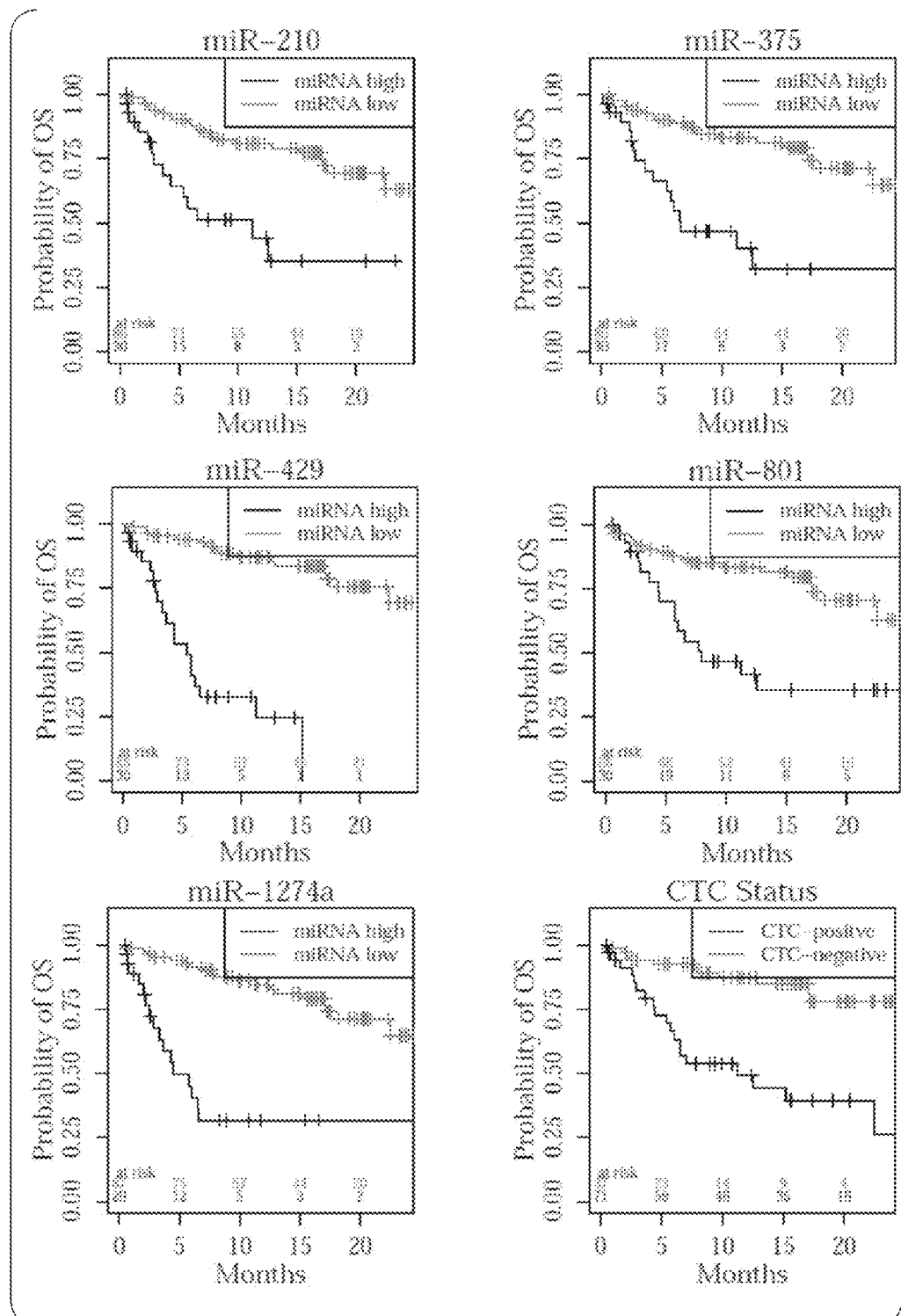

To assess if the prognostic ability of the miRNAs was valid even after therapy, miRNA levels were measured in 117 $MBC_{1C}$ samples. Of the 117 patients tested, 88 patients had progression (79%) and 23 had no progression (21%), while 35 (30%) had died and 81 were still alive (70%). Thus, distribution of both PFS and OS were similar to those of $MBC_{BL}$ samples analyzed. A majority of miRNAs were found still associated with survival and the correlation was found to be, in general, stronger in the MBC1C samples with respect to their P-values (P<0.04 for all, FIG. 3, 4). However, miR-144, miR-215 and miR-801 were no longer significantly correlated to PFS and OS, and miR-365, miR-486-5p and miR-1260 were no longer significantly correlated to OS after therapy (FIG. 11).

Figure 5A:
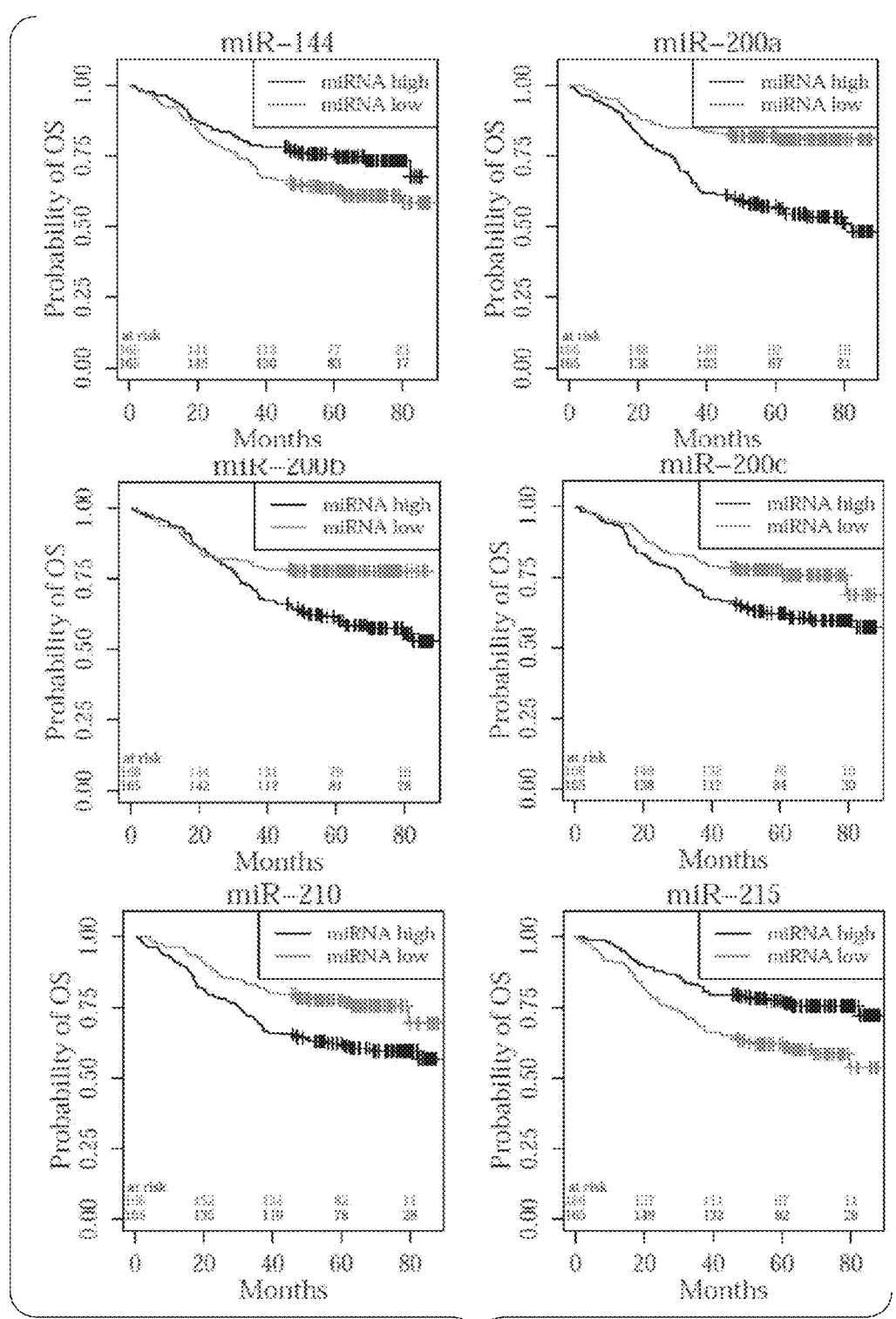
FIGS. 5A-B show Kaplan-Meier curves of miRNAs significantly correlated to OS in all samples of cohort II. Samples dichotomized as less than median and greater than median based on their miRNA levels. Number of individuals at risk in each stratum at different time points is indicated along the x-axis.
Figure 5B:
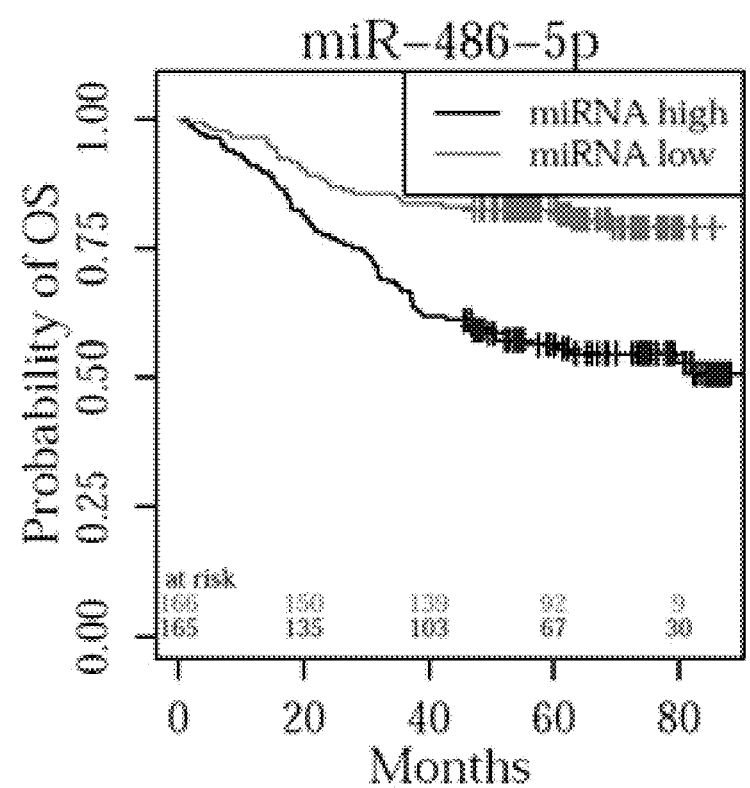

Example 4: Correlation of Circulating miRNAs to Overall Survival Confirmed in an Independent Cohort The 16 miRNAs significantly predicting OS, were interrogated in a second independent cohort which consisted of 335 samples (both M0 and M1) of cohort II. Seven miRNAs, miR-144, miR-200a, miR-200b, miR-200c, miR-210, miR-215, and miR-486-5p were confirmed to predict OS in these samples (P<0.01 for all) (FIG. 5).

Figure 6B:
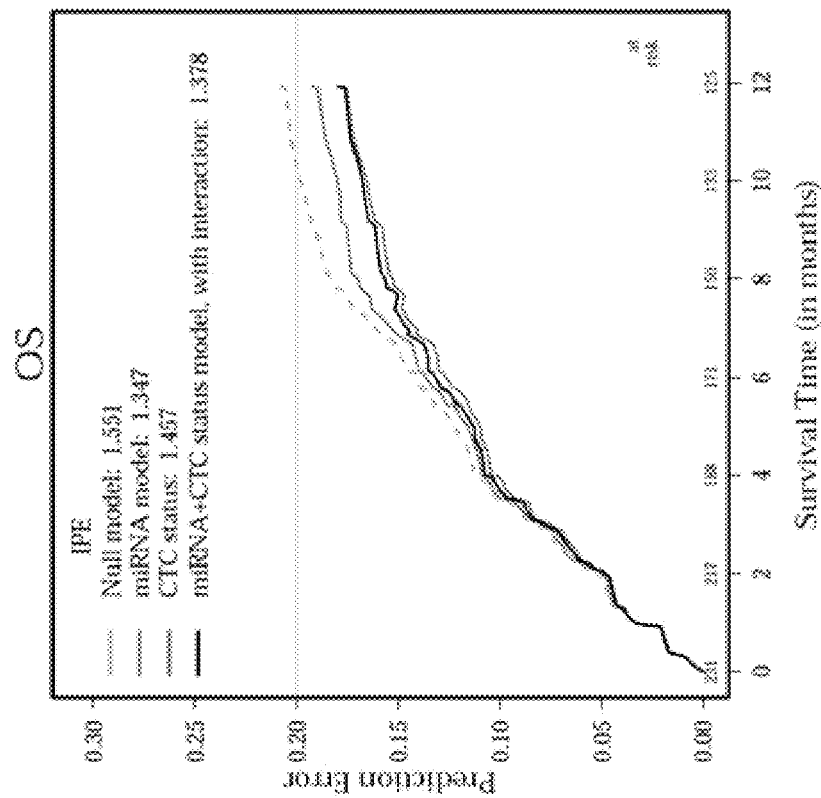
FIGS. 6A-D show integrated prediction error curves (IPEC) shown for null model without co-variates, miRNA model, CTC model, and miRNA+CTC model.
Figure 6A:
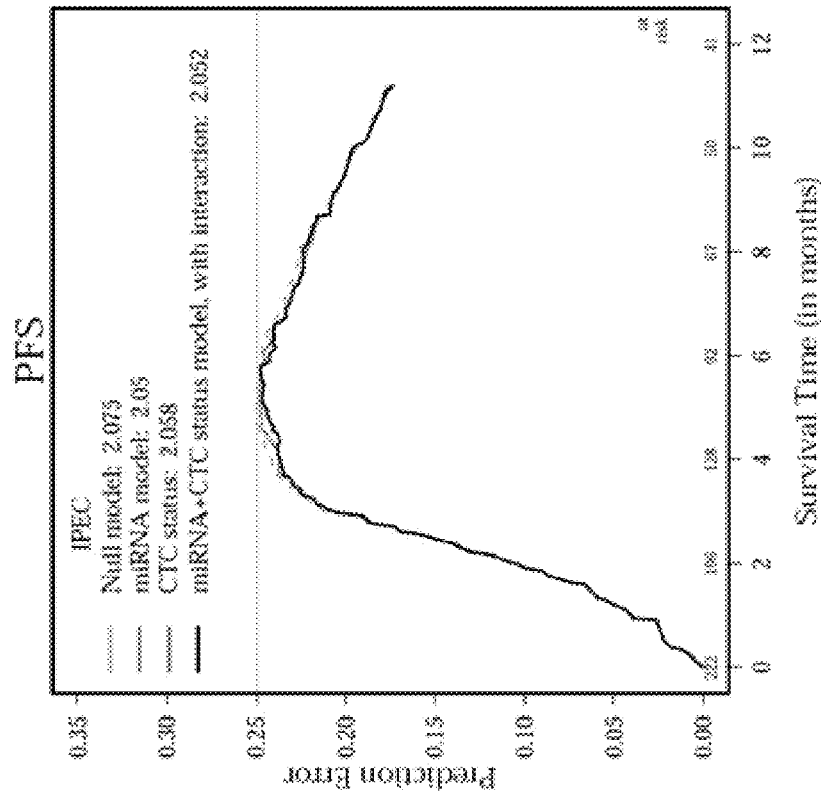
Figure 6D:
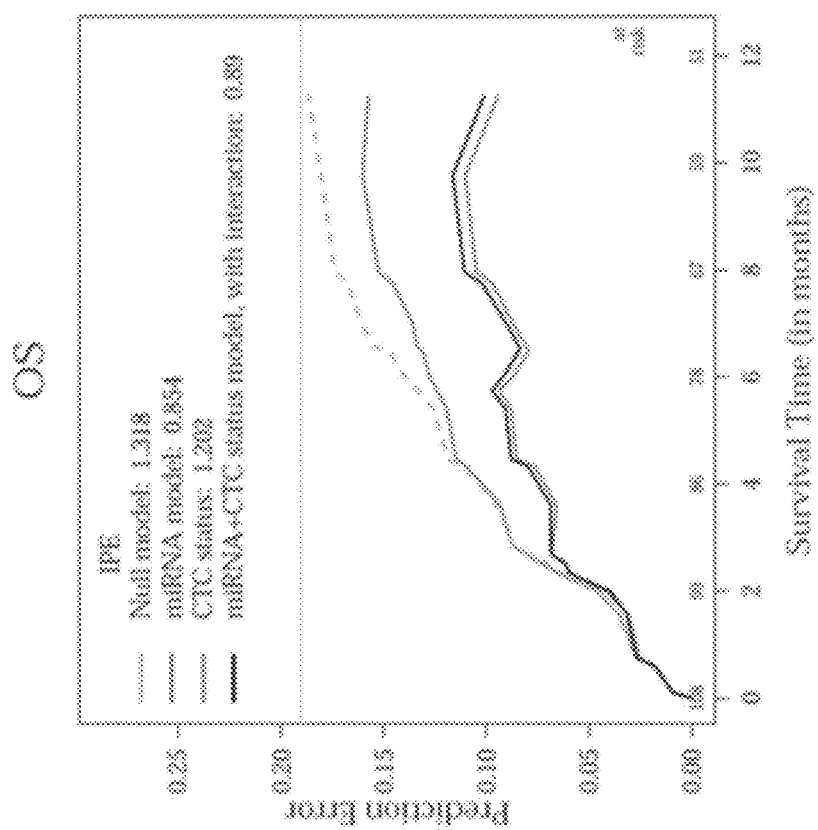
Figure 6C:
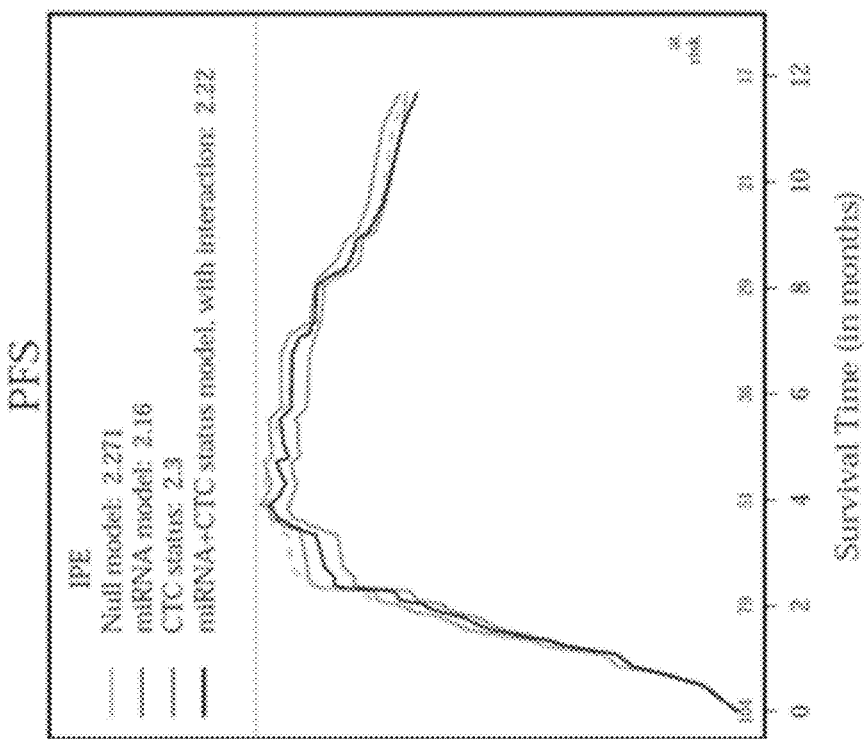

Example 5: Panel of miRNAs Performs Better Than CTC Status miRNA models which had highest predictive power were built with LASSO logistic regression allowing for automatic variable selection with respect to their miRNA levels from both $MBC_{BL}$ and $MBC_{1C}$ samples. In $MBC_{BL}$ sample set, the model contained 10 (miR-141, miR-144, miR-193b, miR-200b, miR-200c, miR-203, miR-215, miR-429, miR-801, and miR-1274a) and 11 miRNAs (miR-141, miR-144, miR-193b, miR-200a, miR-200b, miR-215, miR-429, miR-486-5p, miR-801, miR-1260, and miR-1274a) for PFS and OS, respectively, whereas in $MBC_{1C}$ sample set, the final model consisted of only a small subset of these miRNAs for predicting PFS (miR-141, miR-200c, miR-429, and miR-1274a) and OS (miR-141, miR-200a, miR-200b, miR-429, and miR-1274a) (FIG. 13). While for PFS, miRNA model had only a marginally lower IPEC than CTC status (FIG. 6a), for OS, Cox model with miRNA variables performed significantly better than the model with CTC status (FIG. 6b). The difference between the two models was much more profound in $MBC_{1C}$ sample set (FIG. 6c, 6d). Adding CTC status to the miRNA variables did not improve the accuracy of the miRNA models, with the exception of PFS in $MBC_{BL}$ dataset, wherein unadjusted combination of miRNAs and CTC was proposed as the best model (FIG. 6). In the data set, lung metastasis, visceral metastasis, number of sites of metastasis and PR status of primary tumor was found to be significantly associated with both PFS and OS (data not shown). Comparison of models to predict survival containing these clinical variables with and without the addition of miRNAs demonstrated that addition of miRNAs decreased the prediction error for PFS (IPECS from 1.97 to 1.92) and OS (IPECS 1.47 from 1.30).

Figure 7:
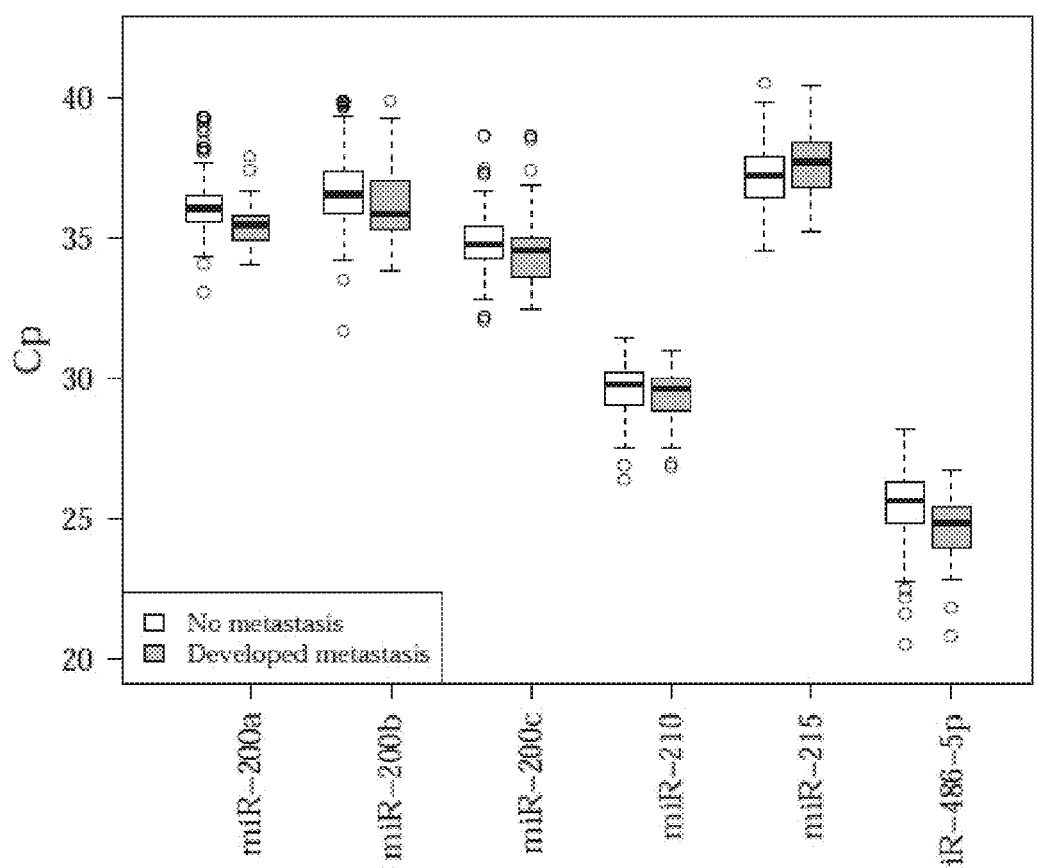
FIG. 7 shows box and whisker plots showing the expression levels of the those miRNAs with significant difference between patients who did not develop metastasis and those who did in the M0 samples from cohort II, represented by crossing point (Cp) values.
Figures 16A, 16B:
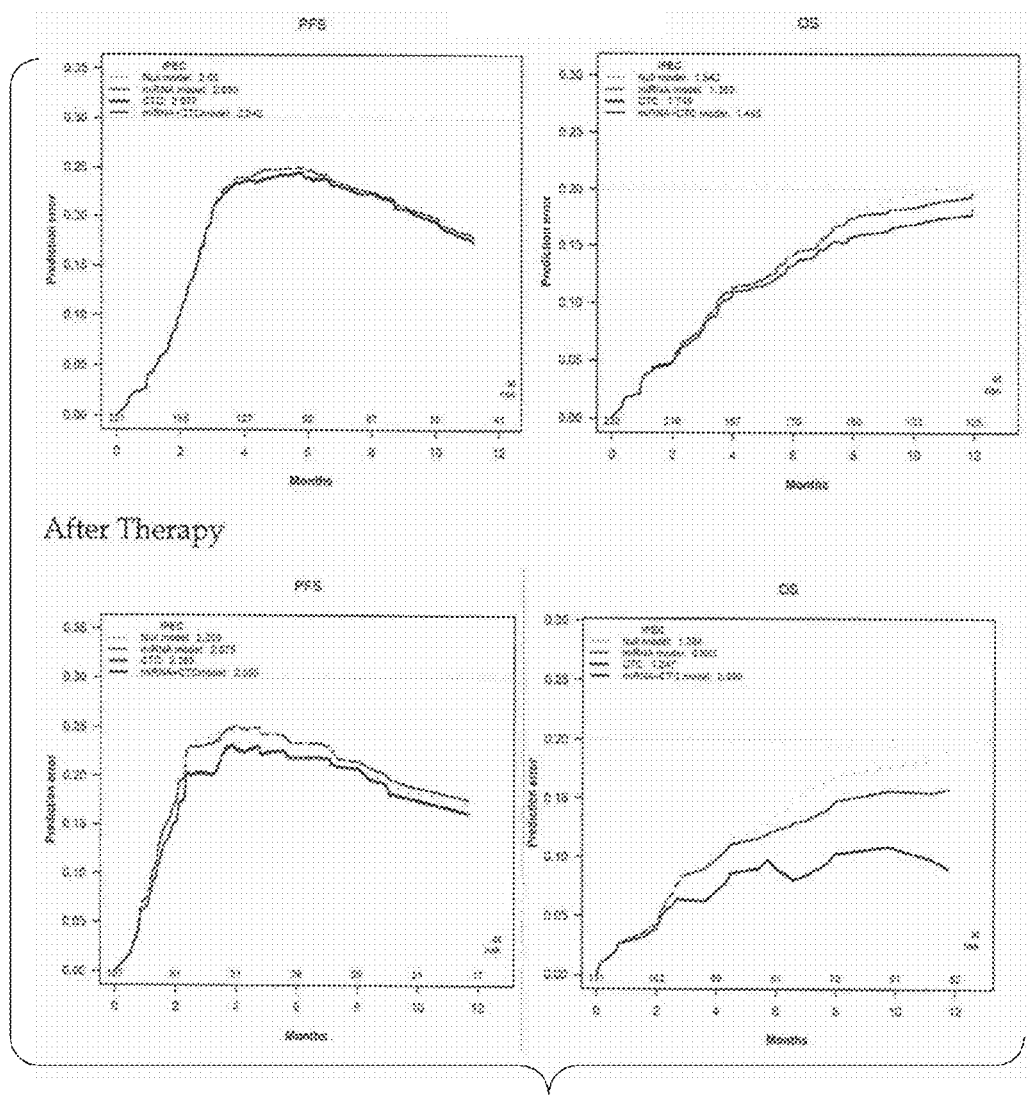
FIGS. 16A-B show comparison of miRNA models with CTC (Circulating tumor cells).

Example 6: Identified Circulating miRNAs can Also Serve as Early Detectors of Metastasis The successfully validated 16 miRNAs were also tested for their relationship to DDFS in M0 samples from Cohort II. Of the 250 subjects 52 (20%) developed metastasis within 2 years and 196 (80%) did not develop metastasis for at least 50 months. The analysis showcased the potential of miR-200a, miR-200b, miR-200c, miR-210, miR-215, and miR-486-5p to correlate to DDFS and thus detect the onset of metastasis even 2 years prior to event (P<0.02) (FIG. 7).

REFERENCES

1. Jemal A, Bray F, Center M M, Ferlay J, Ward E, Forman D. Global cancer statistics. CA Cancer J Clin. 2011; 61:69-90.
2. Cardoso F, Castiglione M, Group EGW Locally recurrent or metastatic breast cancer: ESMO clinical recommendations for diagnosis, treatment and follow-up. Ann Oncol. 2009; 20 Suppl 4:15-8.
3. Lumachi F, Brandes A A, Ermani M, Bruno G, Boccagni P. Sensitivity of serum tumor markers CEA and CA 15-3 in breast cancer recurrences and correlation with different prognostic factors. Anticancer Res. 2000; 20:4751-5.
4. Harris L, Fritsche H, Mennel R, Norton L, Ravdin P, Taube S, et al. American Society of Clinical Oncology 2007 update of recommendations for the use of tumor markers in breast cancer. J Clin Oncol. 2007 November; 25(33):5287-5312.
5. Hanash S M, Baik C S, Kallioniemi O. Emerging molecular biomarkers-blood-based strategies to detect and monitor cancer. Nat Rev Clin Oncol. 2011; 8:142-50.
6. Alix-Panabières C, Pantel K. Technologies for detection of circulating tumor cells: facts and vision. Lab Chip. 2013 October;
7. Largillier R, Ferrero J M, Doyen J, Barriere J, Namer M, Mari V, et al. Prognostic factors in 1,038 women with metastatic breast cancer. Ann Oncol. 2008 December; 19(12):2012-2019.
8. Taneja P, Maglic D, Kai F, Zhu S, Kendig R D, Fry E A, et al. Classical and Novel Prognostic Markers for Breast Cancer and their Clinical Significance. Clin Med Insights Oncol. 2010; 4:15-34.
9. Khanfir A, Lahiani F, Bouzguenda R, Ayedi I, Daoud J, Frikha M. Prognostic factors and survival in metastatic breast cancer: A single institution experience. Reports of Practical Oncology & Radiotherapy. 2013; 18(3):127-132.
10. Chim S S C, Shing T K F, Hung E C W, Leung T Y, Lau T K, Chiu R W K, et al. Detection and characterization of placental microRNAs in maternal plasma. Clin Chem. 2008 March; 54(3):482-490.
11. Turchinovich A, Weiz L, Langheinz A, Burwinkel B. Characterization of extracellular circulating microRNA. Nucleic Acids Research. 2011; 39:7223-33.
12. Zhao H, Shen J, Medico L, Wang D, Ambrosone C B, Liu S. A pilot study of circulating miRNAs as potential biomarkers of early stage breast cancer. PLoS One. 2010; 5(10):e13735.
13. Cuk K, Zucknick M, Heil J, Madhavan D, Schott S, Turchinovich A, et al. Circulating microRNAs in plasma as early detection markers for breast cancer. Int J Cancer. 2013; 132:1602-12.
14. Mar-Aguilar F, Mendoza-Ramírez J A, Malagón-Santiago I, Espino-Silva P K, Santuario-Facio S K, Ruiz-Flores P, et al. Serum circulating microRNA profiling for identification of potential breast cancer biomarkers. Dis Markers. 2013; 34(3):163-169.
15. Cuk K, Zucknick M, Madhavan D, Schott S, Golatta M, Heil J, et al. Plasma MicroRNA Panel for Minimally Invasive Detection of Breast Cancer. PLoS One. 2013; 8(10):e76729.
16. Madhavan D, Cuk K, Burwinkel B, Yang R. Cancer diagnosis and prognosis decoded by bloodbased circulating microRNA signatures. Front Genet. 2013; 4:116.
17. Madhavan D, Zucknick M, Wallwiener M, Cuk K, Modugno C, Scharpff M, et al. Circulating miRNAs as surrogate markers for circulating tumor cells and prognostic markers in metastatic breast cancer. Clin Cancer Res. 2012; 18:5972-82.
18. Roth C, Rack B, Muller V, Janni W, Pantel K, Schwarzenbach H. Circulating microRNAs as bloodbased markers for patients with primary and metastatic breast cancer. Breast Cancer Research. 2010; 12(6):R90.
19. van Schooneveld E, Wouters M C, Van der Auwera I, Peeters D J, Wildiers H, Van Dam P A, et al. Expression profiling of cancerous and normal breast tissues identifies microRNAs that are differentially expressed in serum from patients with (metastatic) breast cancer and healthy volunteers. Breast Cancer Res. 2012; 14(1):R34.
20. Eisenhauer E A, Therasse P, Bogaerts J, Schwartz L H, Sargent D, Ford R, et al. New response evaluation criteria in solid tumours: revised RECIST guideline (version 1.1). Eur J Cancer. 2009 January; 45(2):228-247.
21. Team RDC. R: A language and environment for statistical computing. R foundation for statistical computing, Vienna, Austria. ISBN 3-900051-07-0, URL http://www.R-project.org.; 2010.
22. Dvinge H. HTqPCR—high-throughput qPCR analysis in R and Bioconductor; 2010.
23. Gentleman R, Carey V, Bates D, Bolstad B, Dettling M, Dudoit S, et al. Bioconductor: open software development for computational biology and bioinformatics. Genome Biology. 2004; 5(10):R80.
24. Andersen C L, Jensen J L, Ørntoft T F. Normalization of real-time quantitative reverse transcription-PCR data: a model-based variance estimation approach to identify genes suited for normalization, applied to bladder and colon cancer data sets. Cancer Res. 2004 August; 64(15):5245-5250.
25. Kroh E M, Parkin R K, Mitchell P S, Tewari M. Analysis of circulating microRNA biomarkers in plasma and serum using quantitative reverse transcription-PCR (qRT-PCR). Methods. 2010; 50(4):298-301.
26. Shek L L, Godolphin W. Model for breast cancer survival: relative prognostic roles of axillary nodal status, TNM stage, estrogen receptor concentration, and tumor necrosis. Cancer Res. 1988 October; 48(19):5565-5569.
27. Gregory P A, Bert A G, Paterson E L, Barry S C, Tsykin A, Farshid G, et al. The miR-200 family and miR-205 regulate epithelial to mesenchymal transition by targeting ZEB1 and SIP1. Nat Cell Biol. 2008; 10(5):593-601.
28. Dykxhoorn D M, Wu Y, Xie H, Yu F, Lai A, Petrocca F, et al. miR-200 enhances mouse breast cancer cell colonization to form distant metastases. PLoS ONE. 2009; 4(9):e7181.
29. Viticchié G, Lena A M, Latina A, Formosa A, Gregersen L H, Lund A H, et al. miR-203 controls proliferation, migration and invasive potential of prostate cancer cell lines. Cell Cycle. 2011; 10:1121-1131.

30. Ward A, Balwierz A, Zhang J D, Kublbeck M, Pawitan Y, Hielscher T, et al. Re-expression of microRNA-375 reverses both tamoxifen resistance and accompanying EMT-like properties in breast cancer. Oncogene. 2012 April; 128.
31. Tahiri A, Leivonen S K, Lüders T, Steinfeld I, Ragle Aure M, Geisler J, et al. Deregulation of cancer-related miRNAs is a common event in both benign and malignant human breast tumors. Carcinogenesis. 2013 November;
32. Yan L X, Huang X F, Shao Q, Huang M Y, Deng L, Wu Q L, et al. MicroRNA miR-21 overexpression in human breast cancer is associated with advanced clinical stage, lymph node metastasis and patient poor prognosis. RNA. 2008 November; 14(11):2348-2360.
33. Nie J, Liu L, Zheng W, Chen L, Wu X, Xu Y, et al. microRNA-365, down-regulated in colon cancer, inhibits cell cycle progression and promotes apoptosis of colon cancer cells by probably targeting Cyclin D1 and Bcl-2. Carcinogenesis. 2012 January; 33(1):220-225.
34. Kang S M, Lee H J, Cho J Y. MicroRNA-365 regulates NKX2-1, a key mediator of lung cancer. Cancer Lett. 2013 July; 335(2):487-494.
35. Wang K, Yuan Y, Cho J H, McClarty S, Baxter D, Galas D J. Comparing the MicroRNA spectrum between serum and plasma. PLoS One. 2012; 7(7):e41561.
36. Turchinovich A, Burwinkel B. Distinct AGO1 and AGO2 associated miRNA profiles in human cells and blood plasma. RNA Biol. 2012 August; 9(8):1066-1075.

The invention claimed is:

1. A non-invasive method for the prediction of the onset of metastasis in a primary breast cancer patient or the progression-free survival (PFS) or overall survival (OS) of a patient with metastatic breast cancer, comprising:

(a) providing a biological sample from a primary breast cancer patient or a patient with metastatic breast cancer;

(b) analyzing the biological sample to determine the amount of at least one miRNA;

(c) normalizing the amount of the at least one miRNA to an endogenous control comprising miR-29a and/or miR-139-5p;

wherein:

an increased level of miR-144, miR-215, miR-486-5p, or any combination thereof is indicative of increased OS of the patient with metastatic breast cancer;

a decreased level of miR-141, miR-193b, miR-200a, miR-200b, miR-200c, miR-203, miR-210, miR-365, miR-375, miR-429, miR-801, miR-1260, miR-1274a, or any combination thereof is indicative of increased OS of the patient with metastatic breast cancer;

an increased level of miR-144, miR-215, or a combination thereof is indicative of increased PFS of the patient with metastatic breast cancer;

a decreased level of miR-141, miR-193b, miR-200a, miR-200b, miR-200c, miR-203, miR-375, miR-429, miR-1274a, or any combination thereof is indicative of increased PFS of the patient with metastatic breast cancer;

an increased level of miR-200a, miR-200b, miR-200c, miR-210, miR-486-5p, or any combination thereof is indicative of an increased risk of the onset of metastasis in the primary breast cancer patient; and/or a decreased level of miR-215 is indicative of an increased risk of the onset of metastasis in the primary breast cancer patient.

2. The method of claim 1, wherein the biological sample is peripheral blood or derivative thereof.

3. The method of claim 1, wherein said metastatic breast cancer also includes metastasis in visceral and non-visceral organs.

4. A method for monitoring the therapy of a patient being treated against primary breast cancer or metastatic breast cancer comprising:
  (a) providing a biological sample from said patient and
  (b) predicting the onset of metastasis in a primary breast cancer patient or the progression-free survival (PFS) or overall survival (OS) of a patient with metastatic breast cancer according to claim 1, wherein the predicting step is used to indicate the effectiveness of a treatment that the subject is undergoing, and
  (c) optionally adjusting the treatment.

5. The method of claim 1, further comprising administering to the primary breast cancer patient or the patient with metastatic breast cancer a pharmaceutical composition comprising an effective amount of an anti-cancer agent with a dosage regime adapted for the prevention, amelioration or treatment of the onset of metastasis in a primary breast cancer.

6. The method of claim 2, wherein the biological sample is plasma.

7. The method of claim 3, wherein the visceral and non-visceral organ are selected from the group consisting of the bone, lungs, regional lymph nodes, liver, brain and any combination thereof.

8. The method of claim 1, wherein analysing the biological sample includes a quantitative PCR assay.

9. The method of claim 1, wherein the normalizing step further comprises an exogenous control comprising cel miR 39.

* * * * *